United States Patent
Bradbury et al.

(10) Patent No.: US 8,168,411 B2
(45) Date of Patent: May 1, 2012

(54) HIGHLY THERMOSTABLE FLUORESCENT PROTEINS

(75) Inventors: Andrew M. Bradbury, Santa Fe, NM (US); Geoffrey S. Waldo, Santa Fe, NM (US); Csaba Kiss, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/306,735

(22) Filed: Nov. 29, 2011

(65) Prior Publication Data

US 2012/0077266 A1  Mar. 29, 2012

Related U.S. Application Data

(62) Division of application No. 13/023,421, filed on Feb. 8, 2011, now Pat. No. 8,067,541, which is a division of application No. 12/317,185, filed on Dec. 19, 2008, now Pat. No. 7,910,700.

(60) Provisional application No. 61/008,689, filed on Dec. 21, 2007.

(51) Int. Cl.
C12P 21/06 (2006.01)
C12N 1/20 (2006.01)
C12N 15/00 (2006.01)
C07H 21/02 (2006.01)

(52) U.S. Cl. ............... 435/69.1; 435/252.33; 435/320.1; 536/23.1

(58) Field of Classification Search ........................ None
See application file for complete search history.

*Primary Examiner* — Nashaat Nashed
(74) *Attorney, Agent, or Firm* — Bruce H. Cottrell; Kenneth K. Sharples; Meredith H. Schoenfeld

(57) ABSTRACT

Thermostable fluorescent proteins (TSFPs), methods for generating these and other stability-enhanced proteins, polynucleotides encoding such proteins, and assays and method for using the TSFPs and TSFP-encoding nucleic acid molecules are provided. The TSFPs of the invention show extremely enhanced levels of stability and thermotolerance. In one case, for example, a TSFP of the invention is so stable it can be heated to 99° C. for short periods of time without denaturing, and retains 85% of its fluorescence when heated to 80° C. for several minutes. The invention also provides a method for generating stability-enhanced variants of a protein, including but not limited to fluorescent proteins.

13 Claims, 26 Drawing Sheets

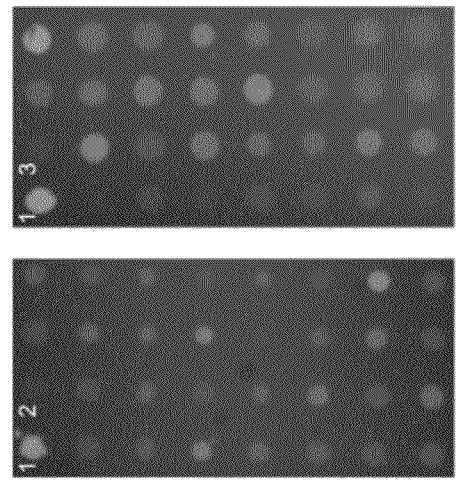
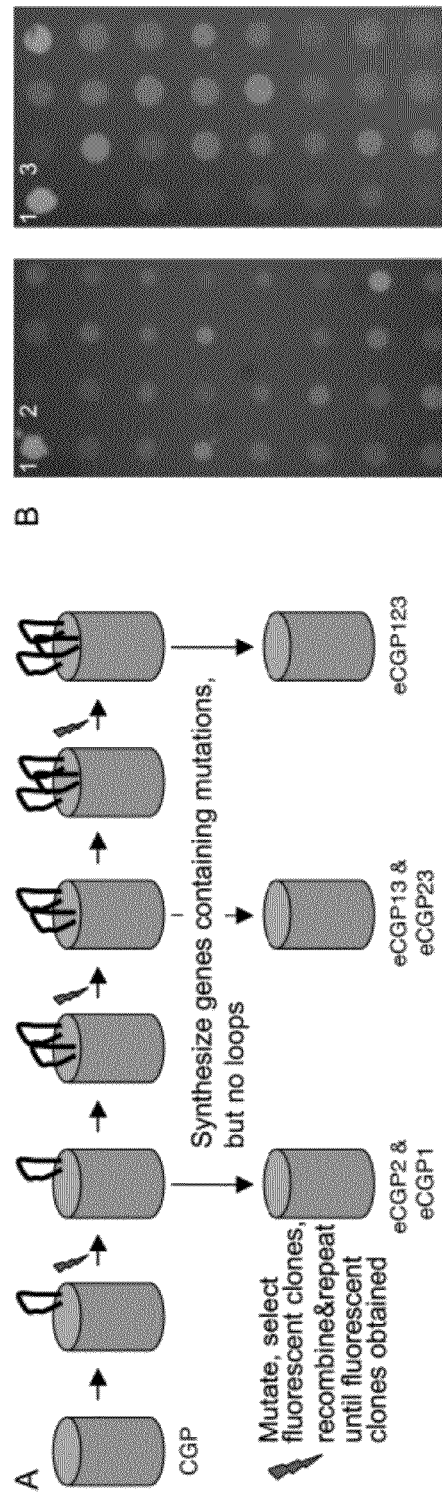
Figure 1: evolutionary strategy

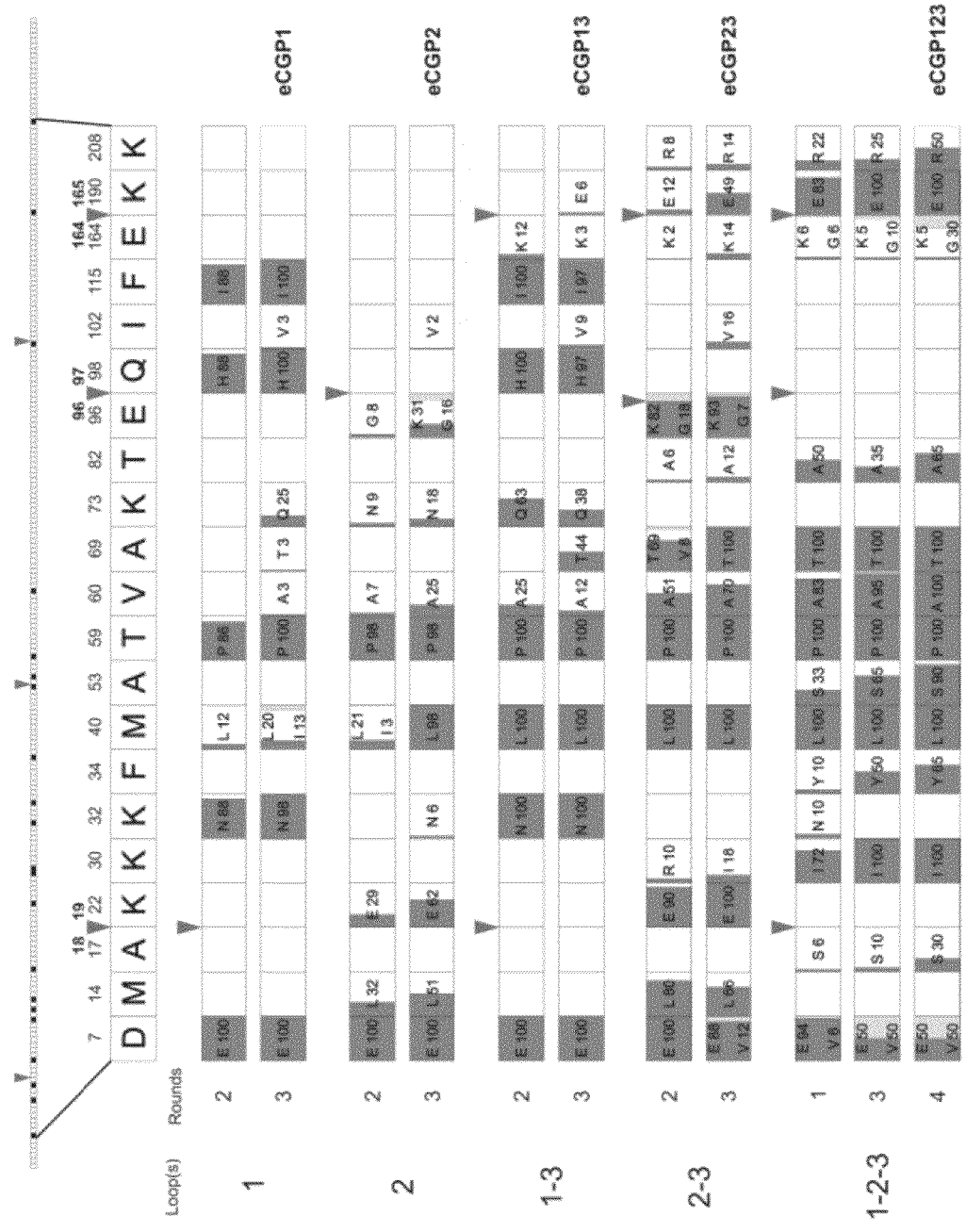
Figure 2: Mutations observed during evolution

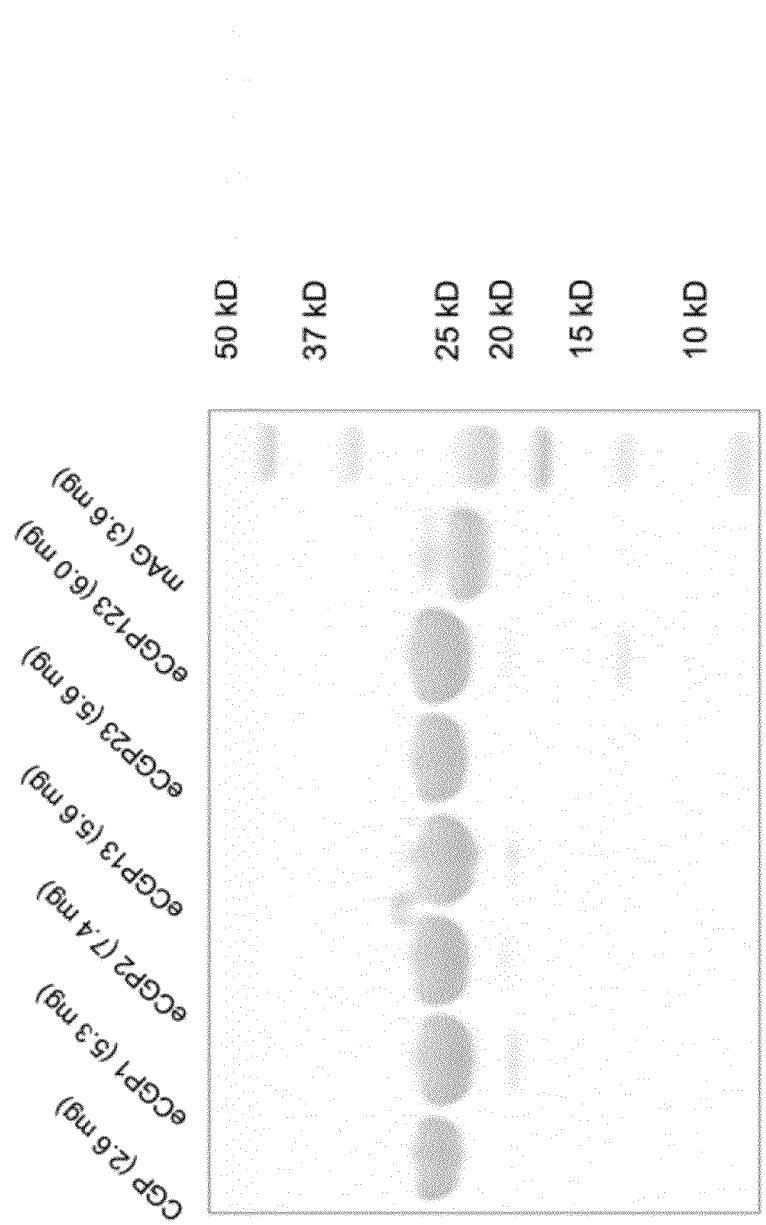
Figure 4A: expression and purification of evolved fluorescent proteins

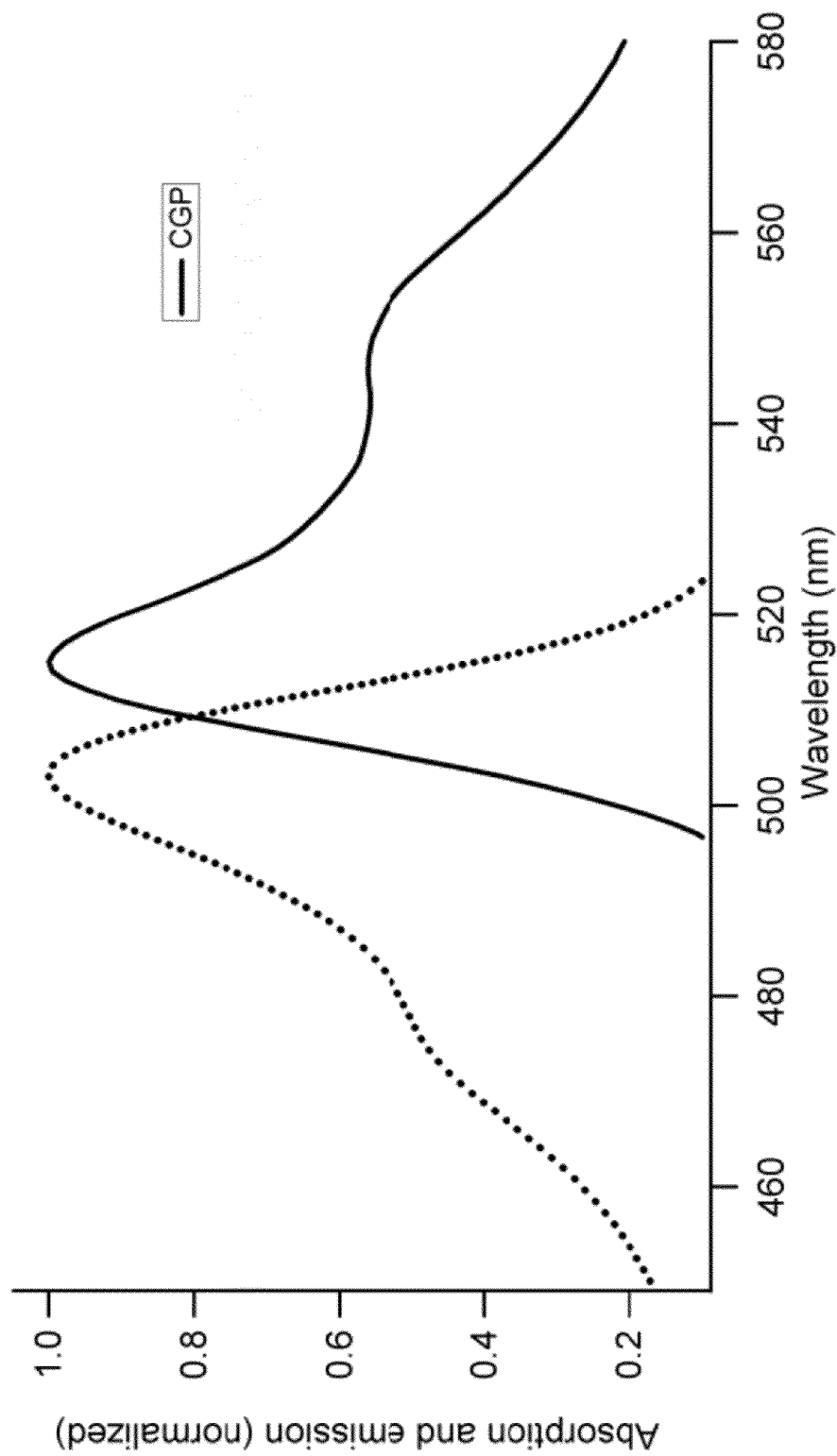
Figure 4B-i: excitation emission of CGP

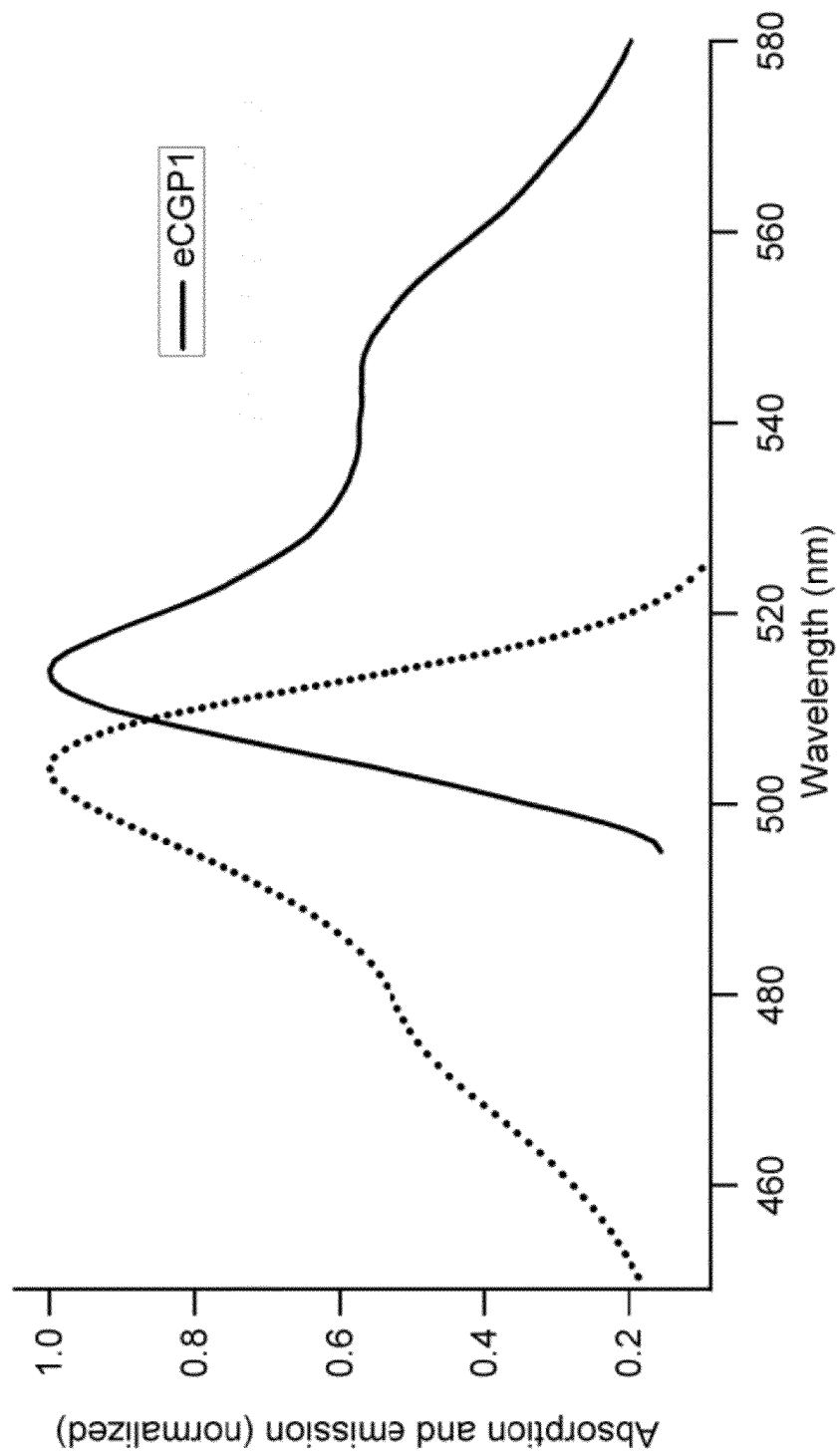

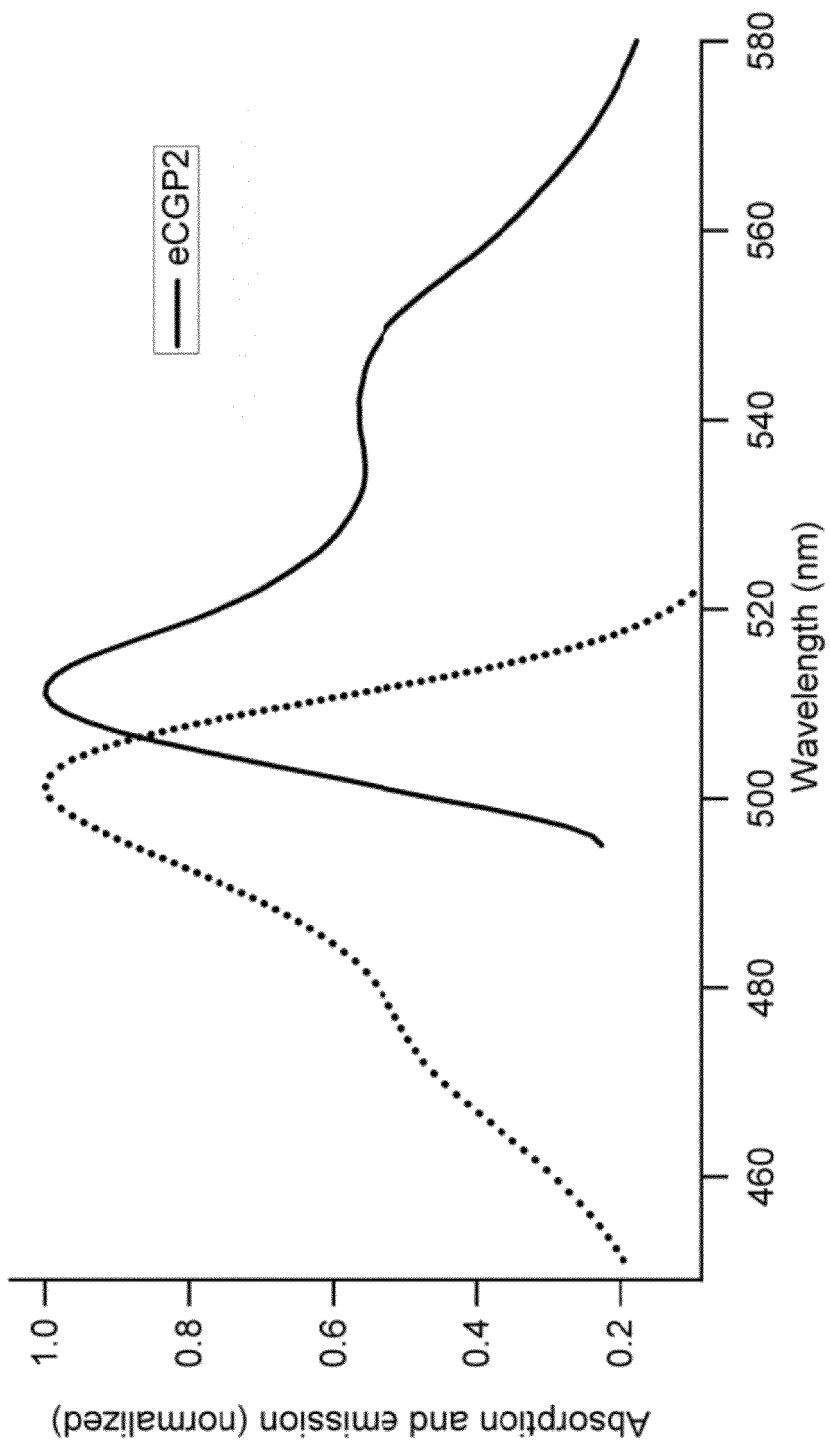

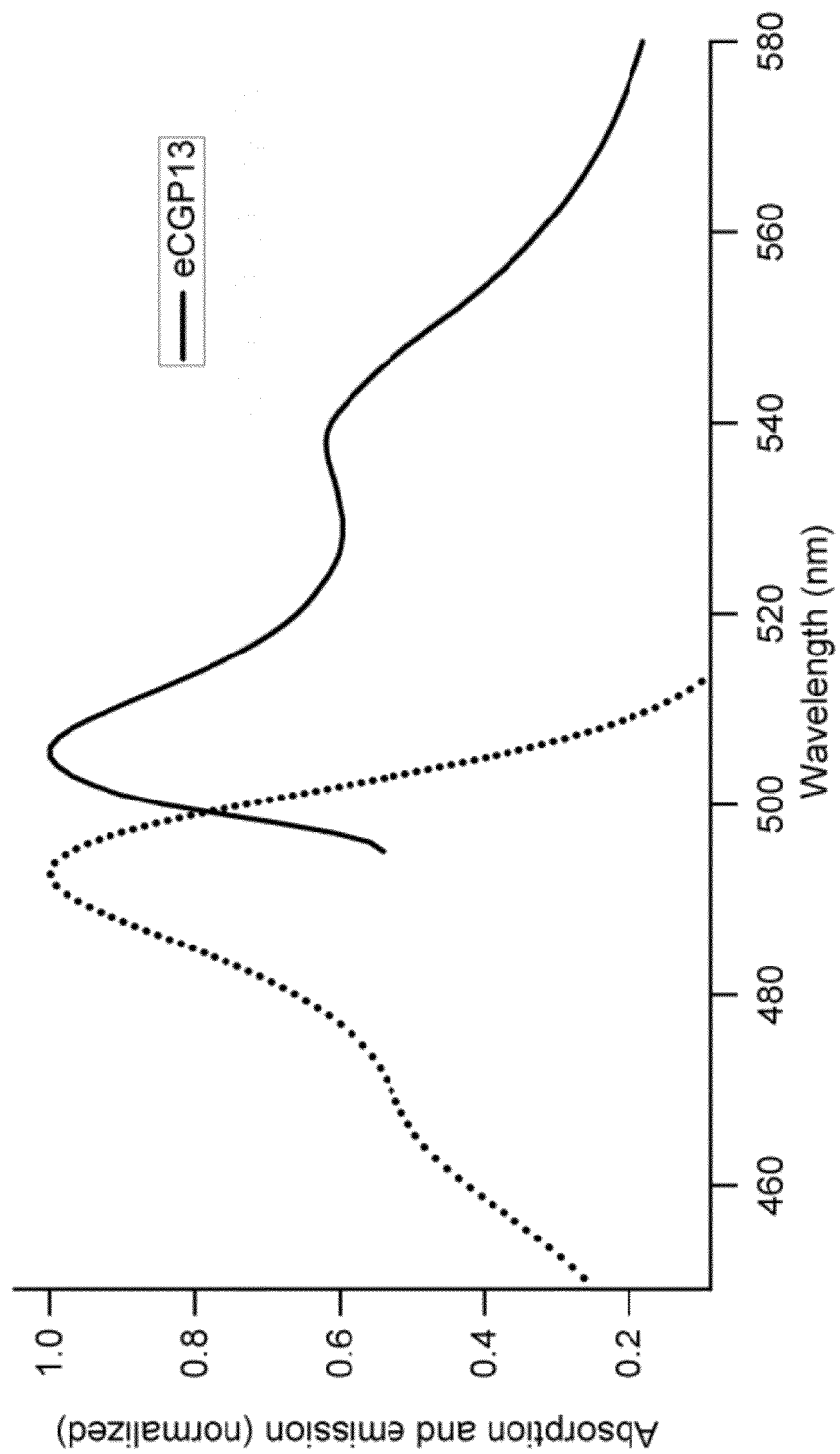

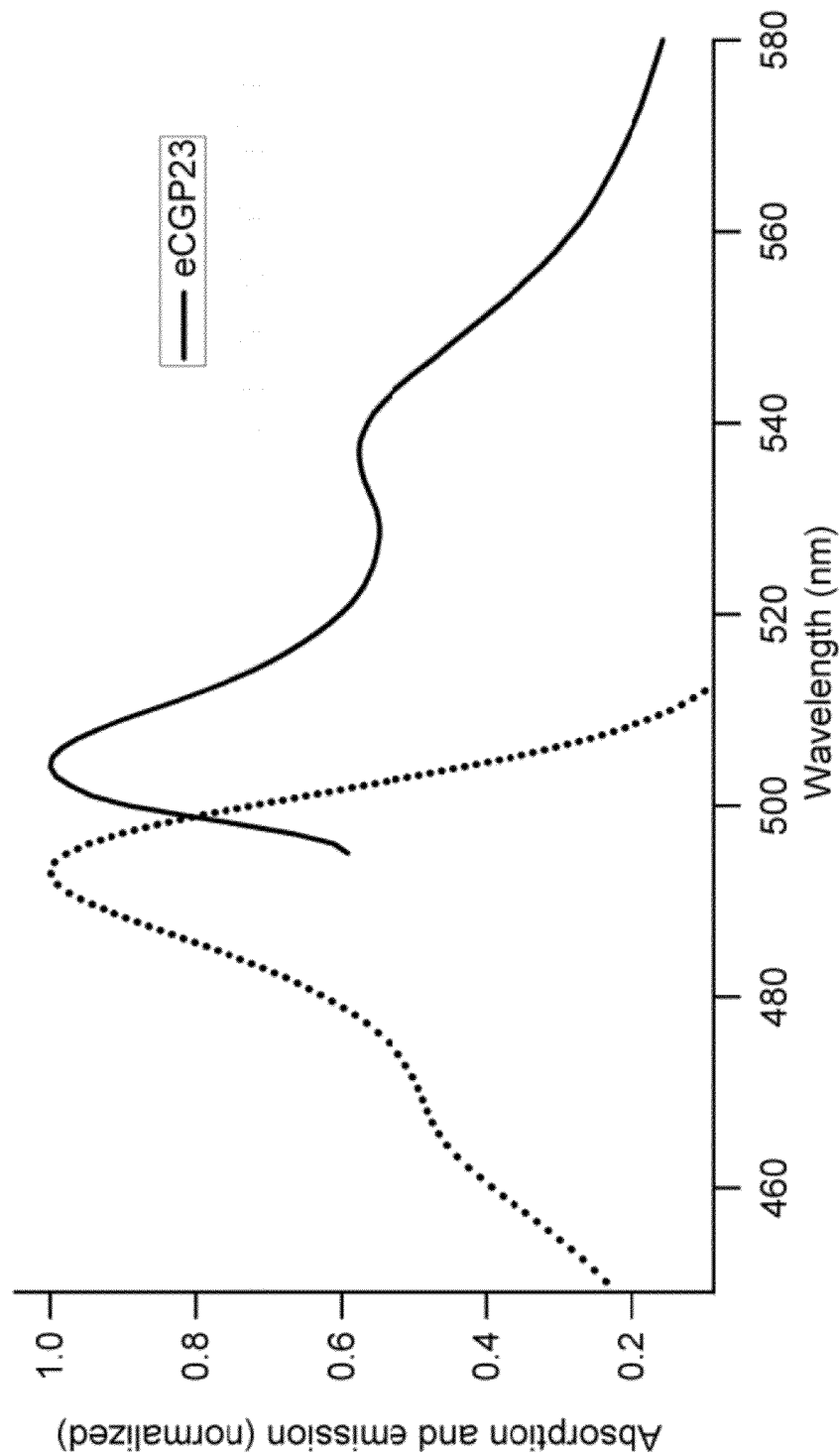
Figure 4B-v: excitation emission of eCGP23

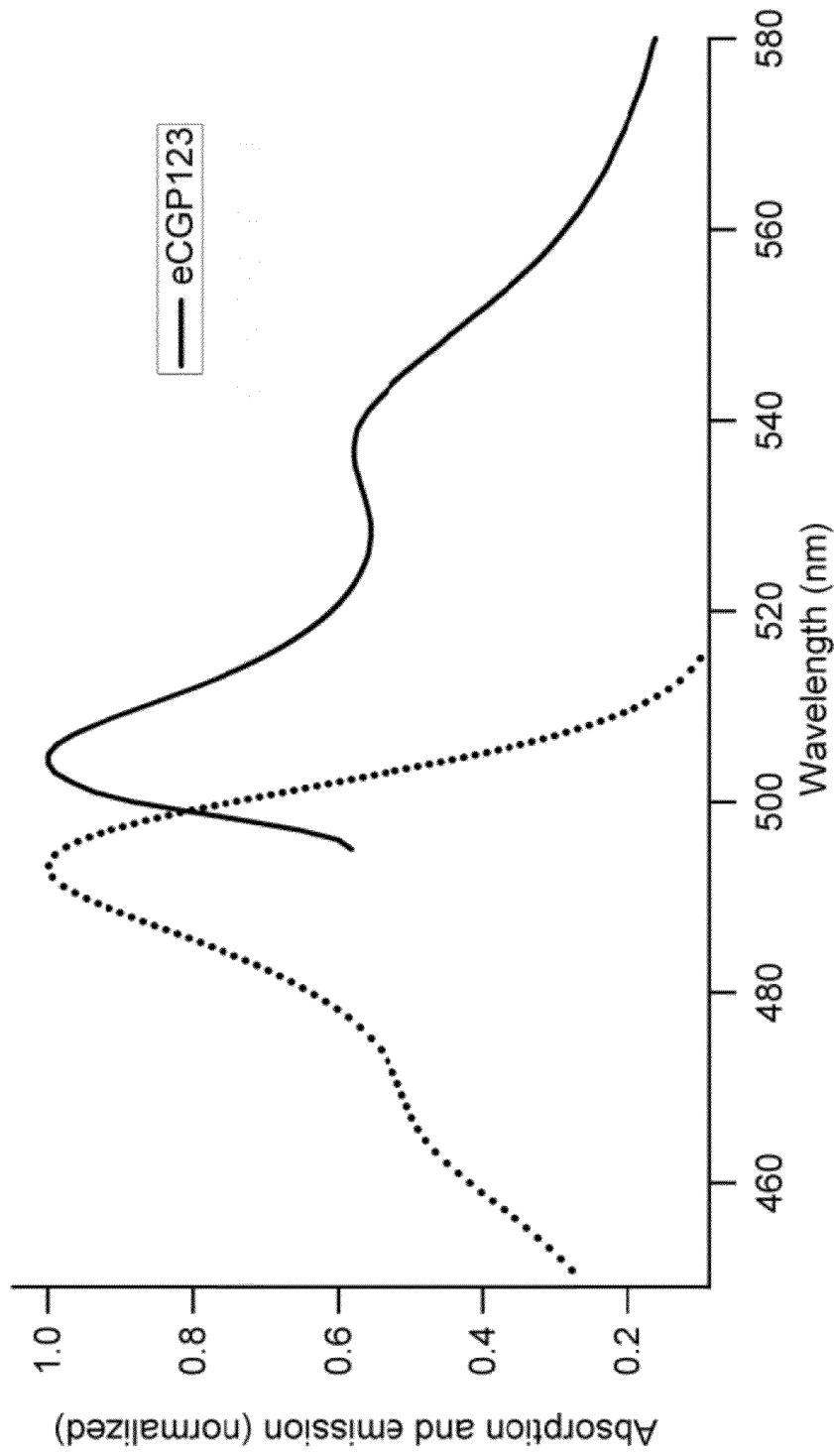

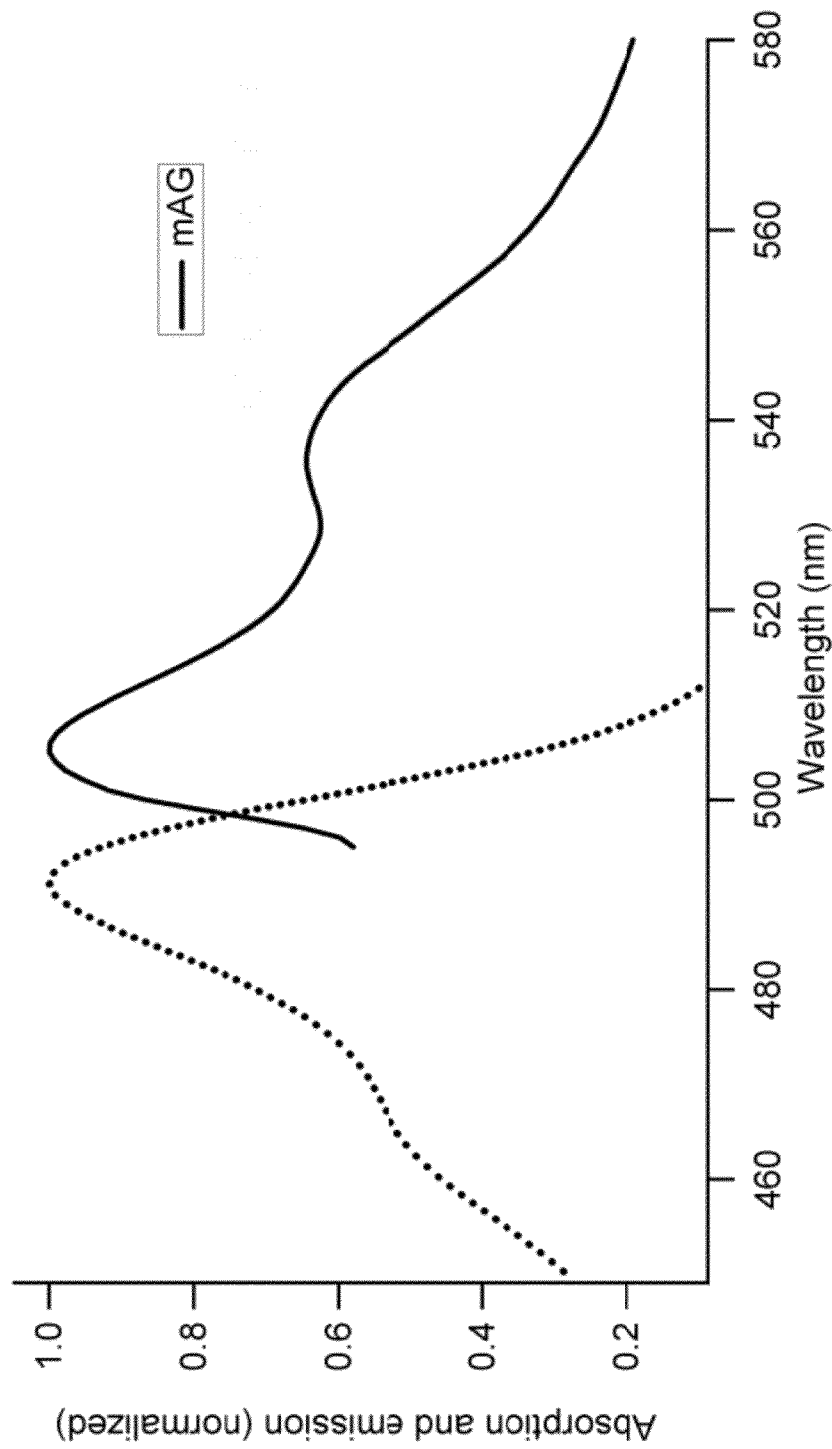

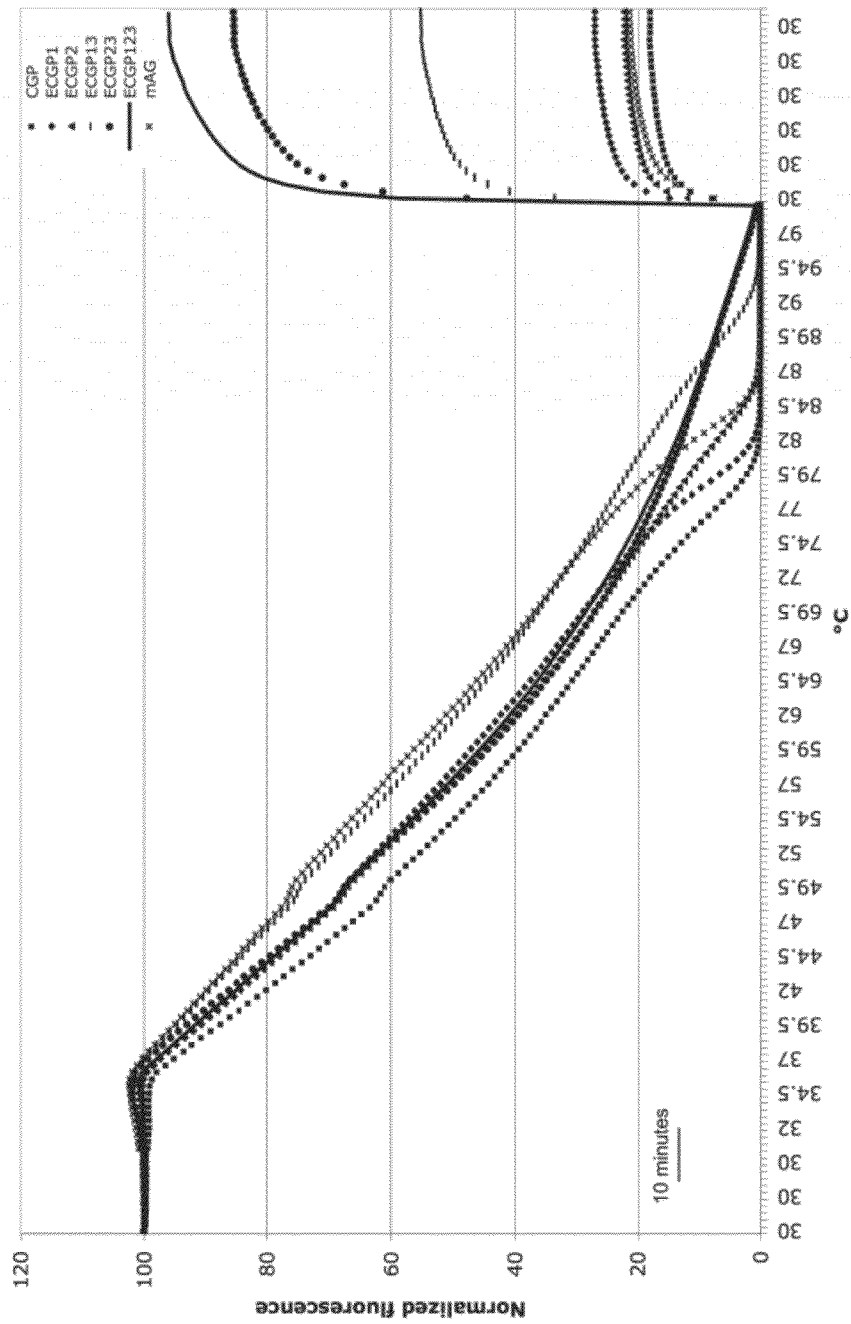

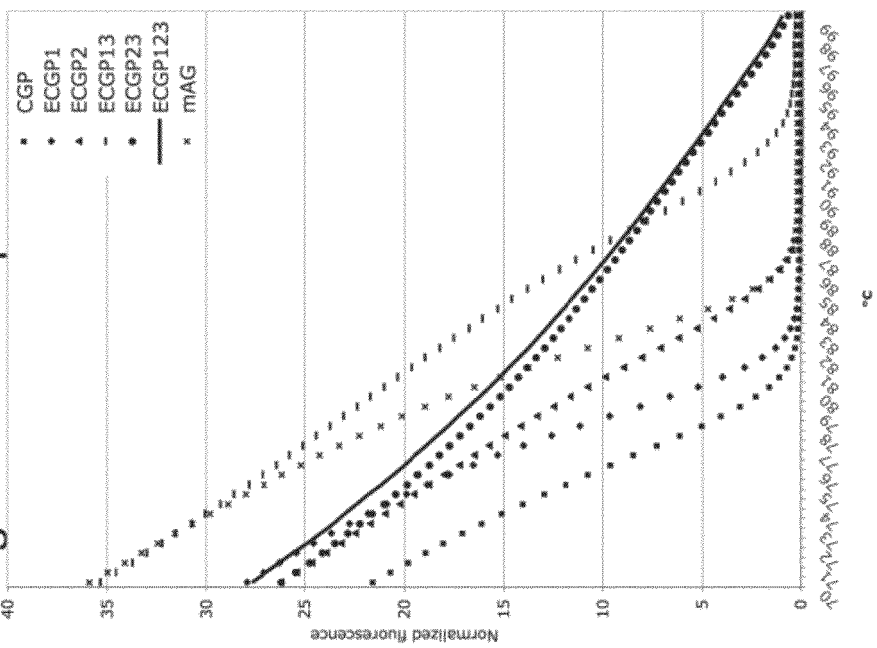

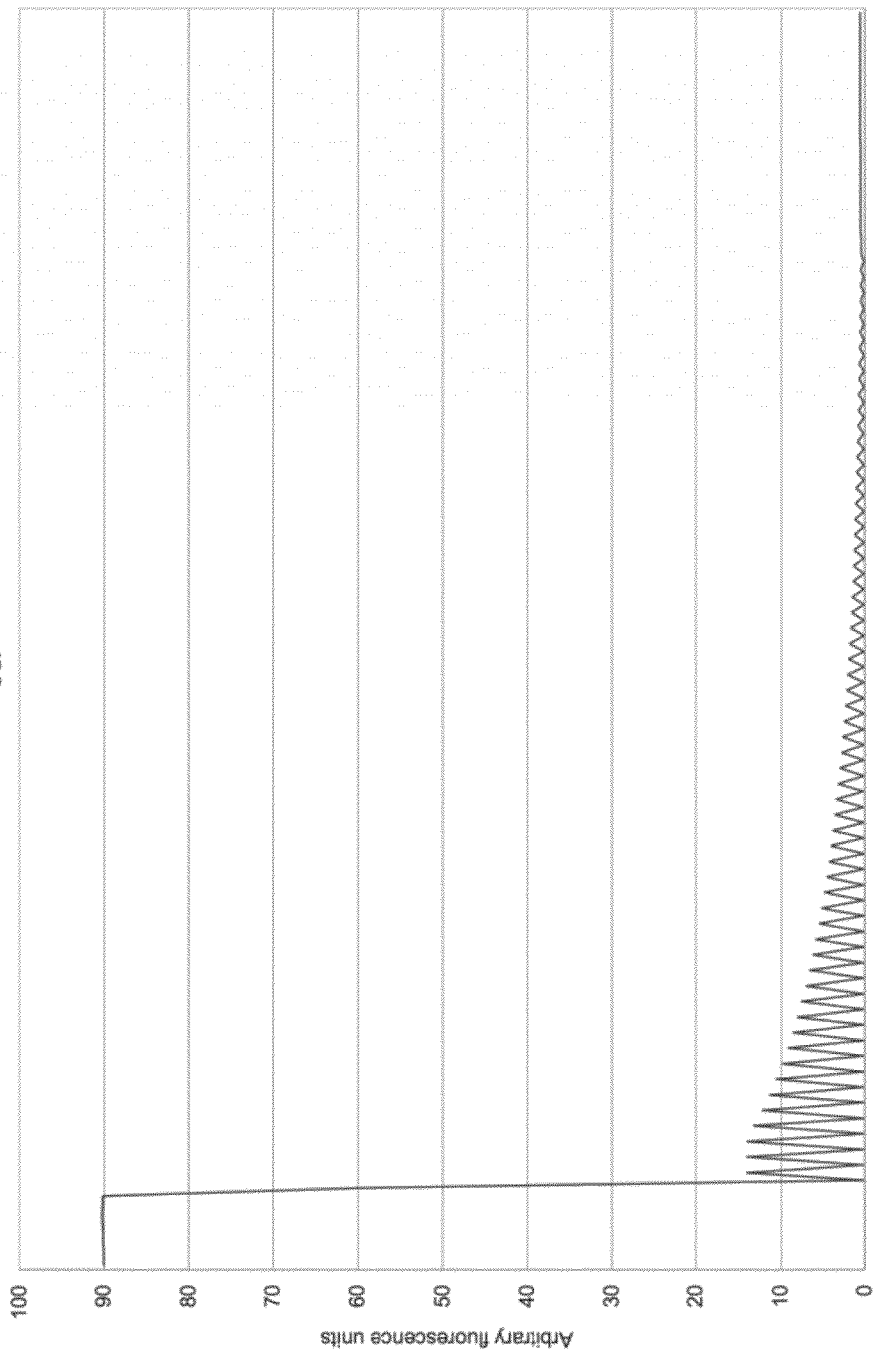

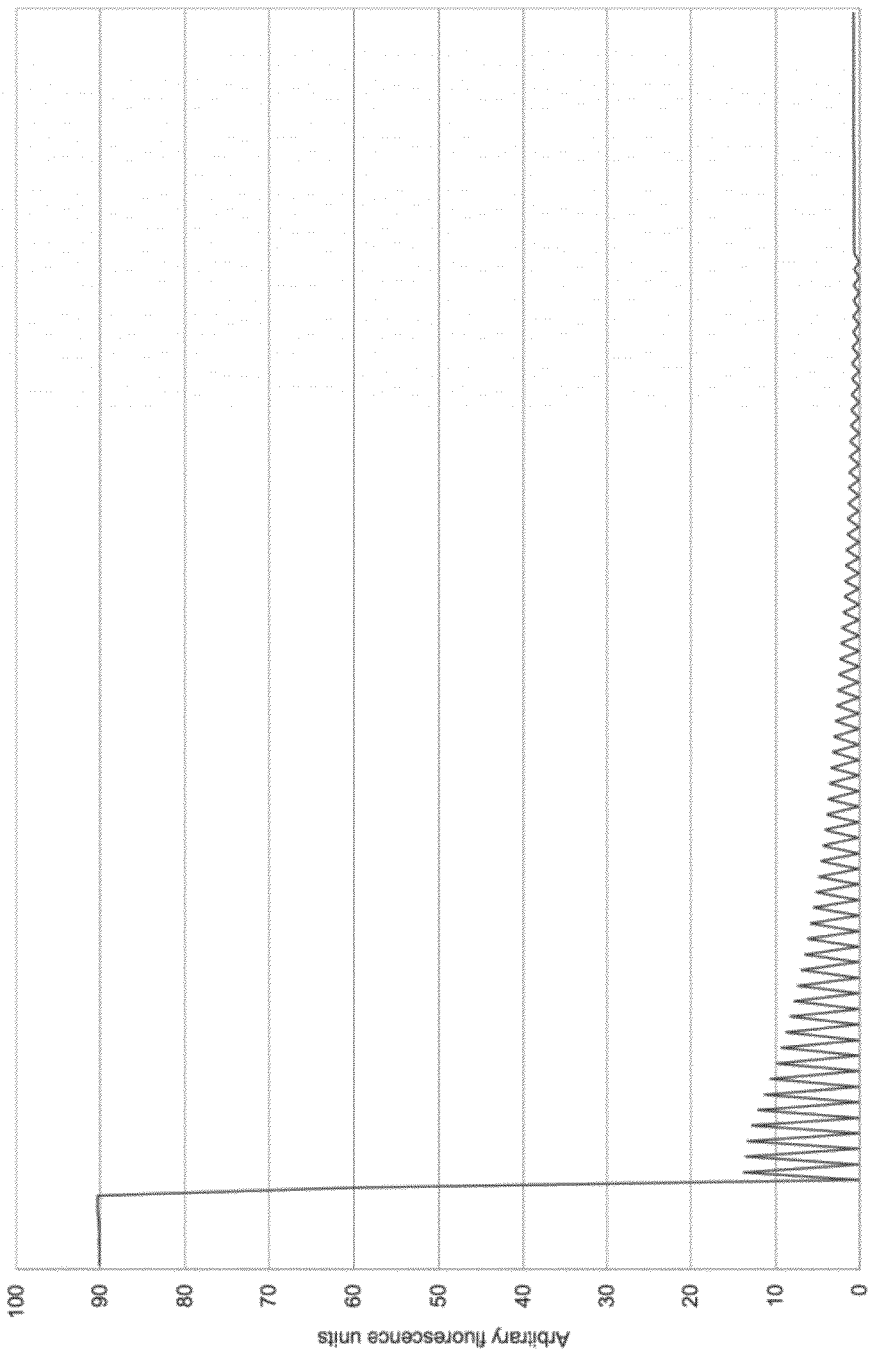

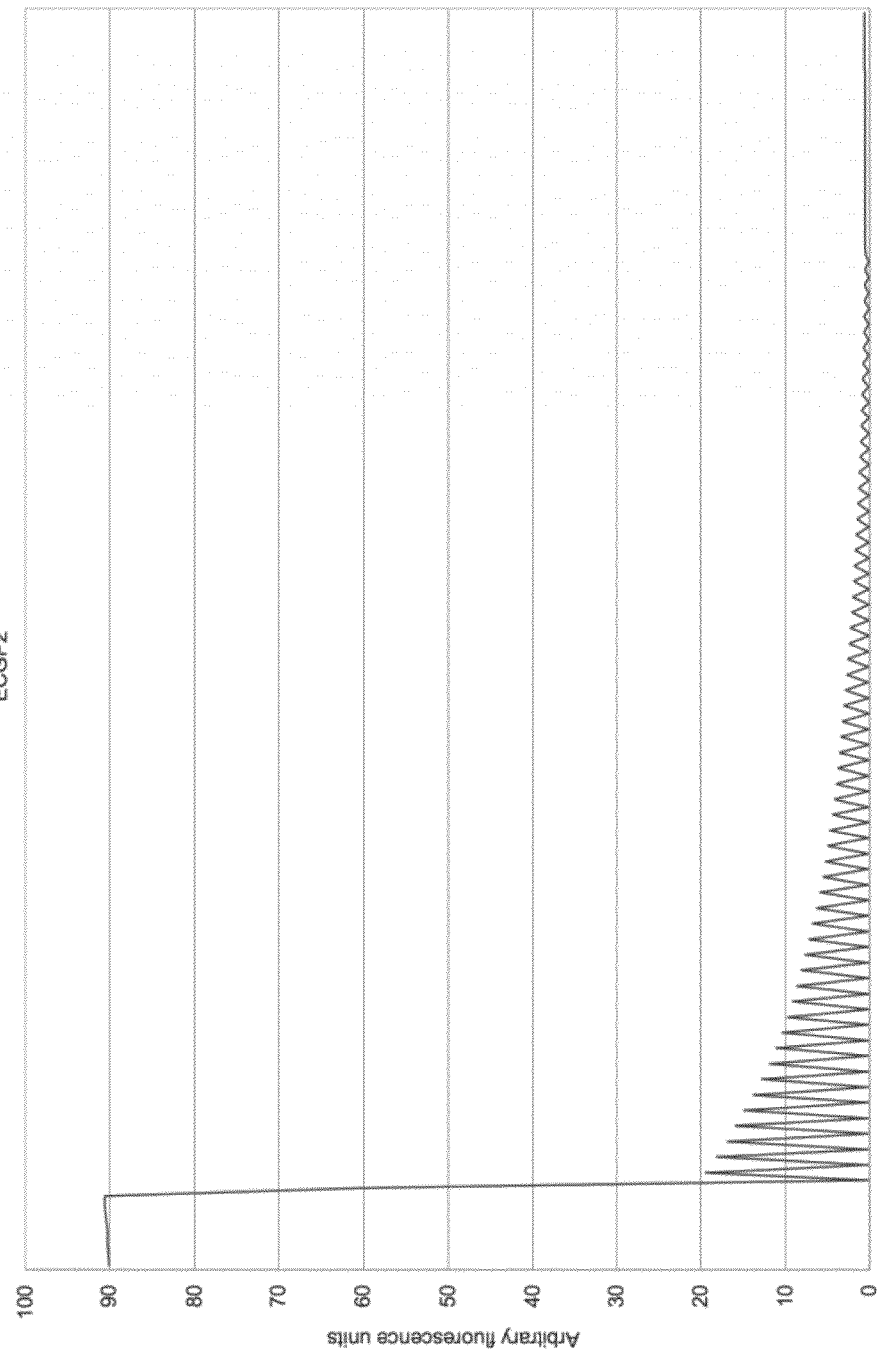

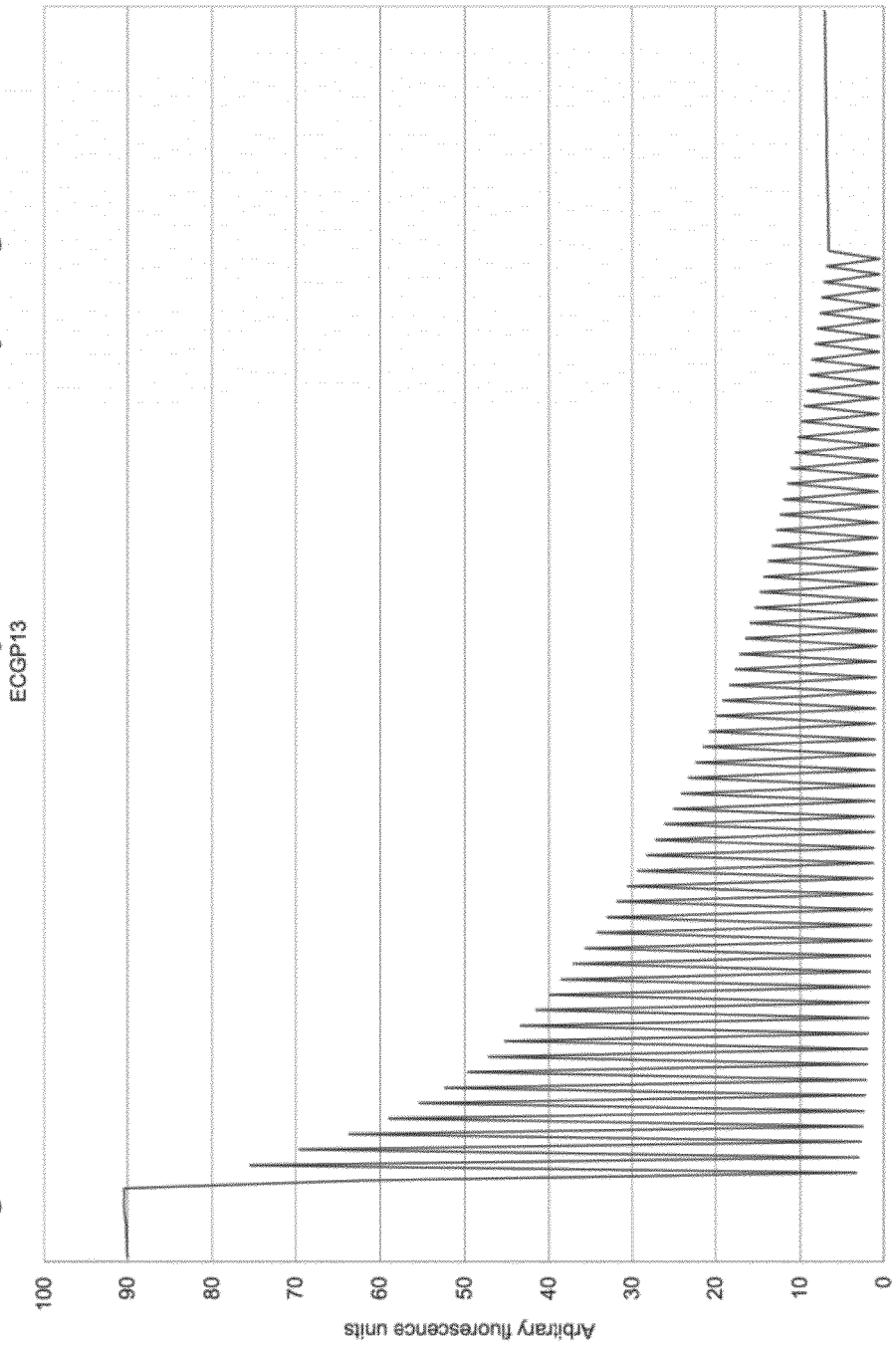

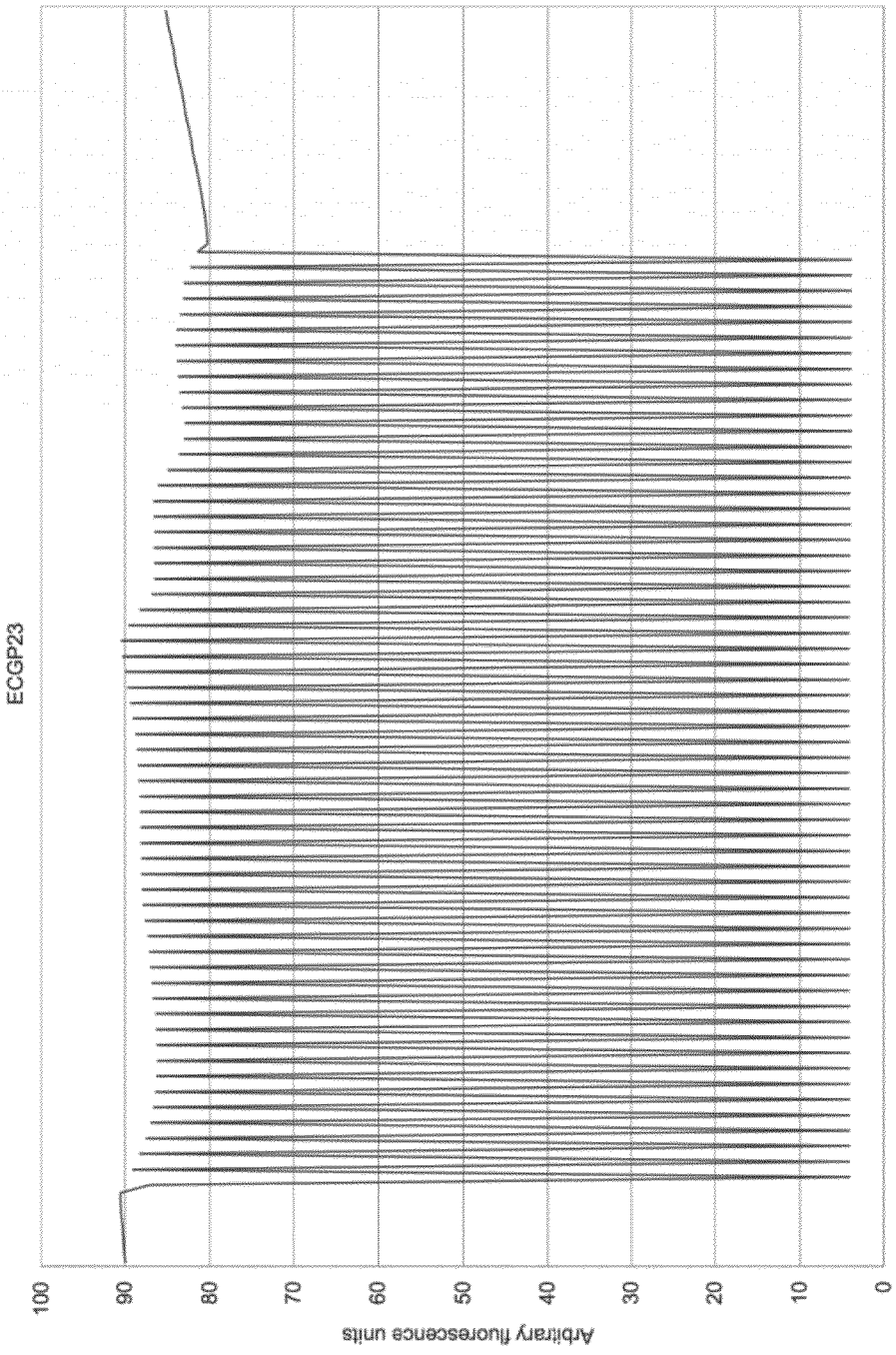

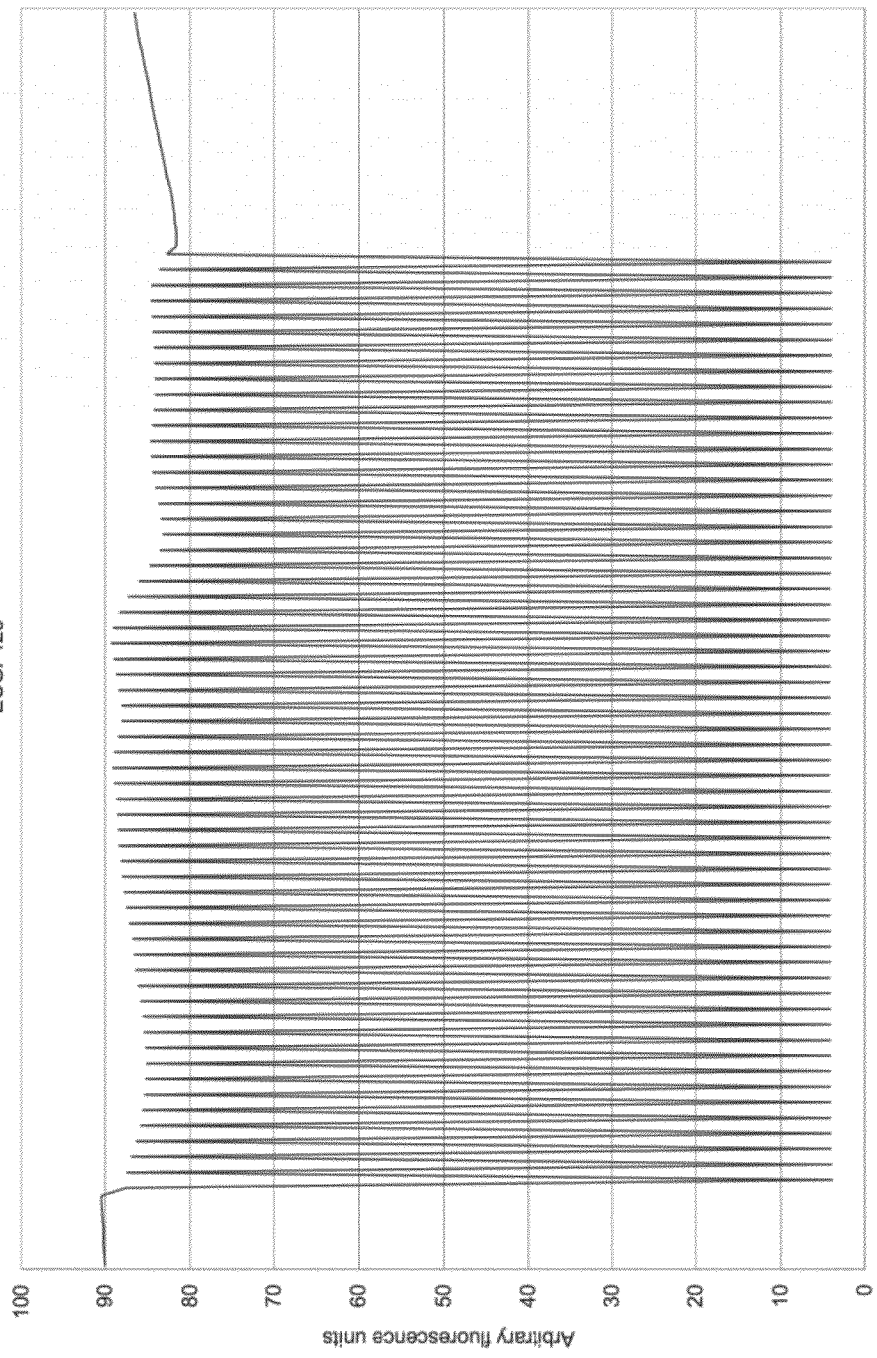

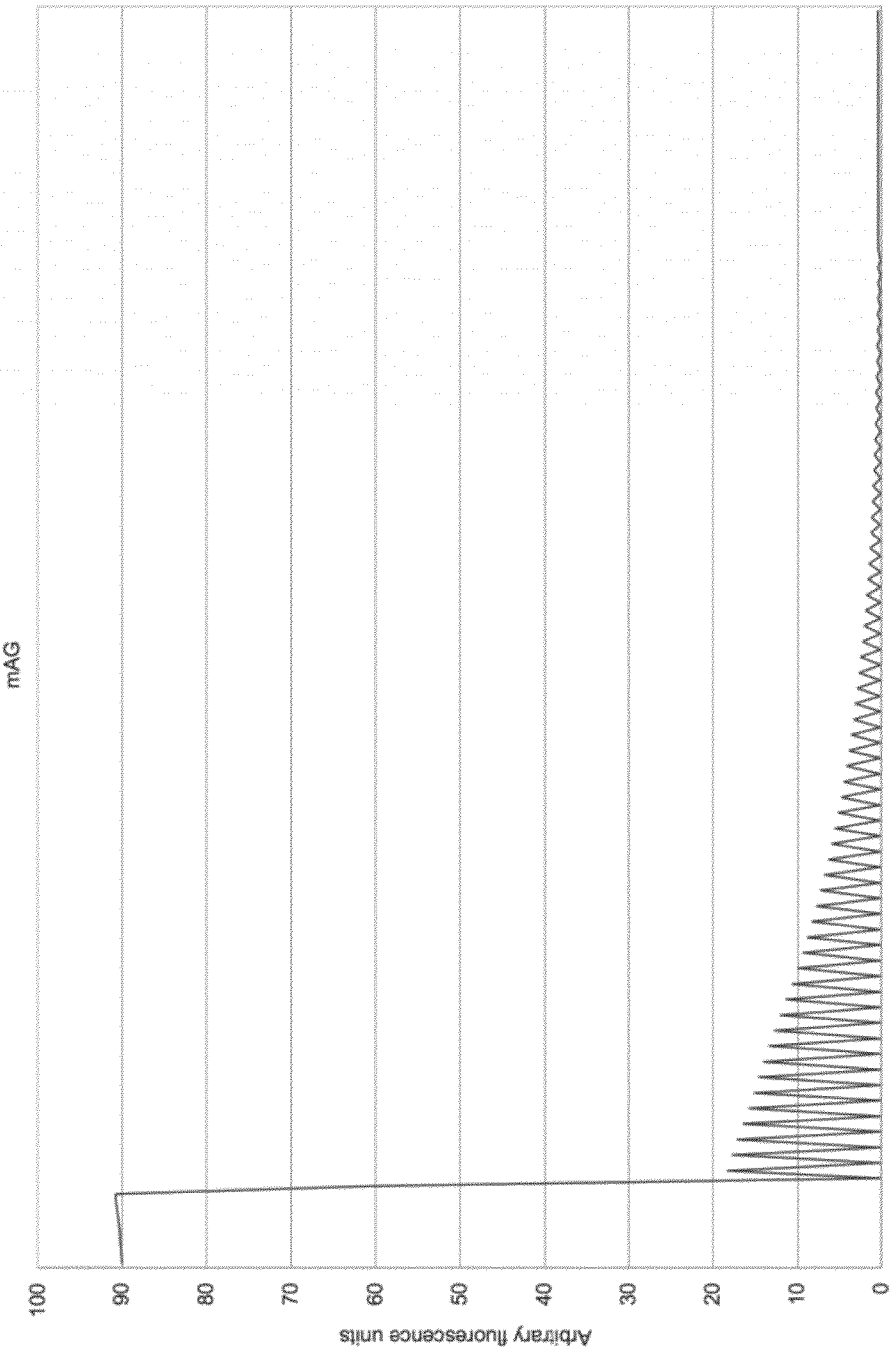

Figure 5D: Fluorescence loss in the first few minutes at 80°C and normalization

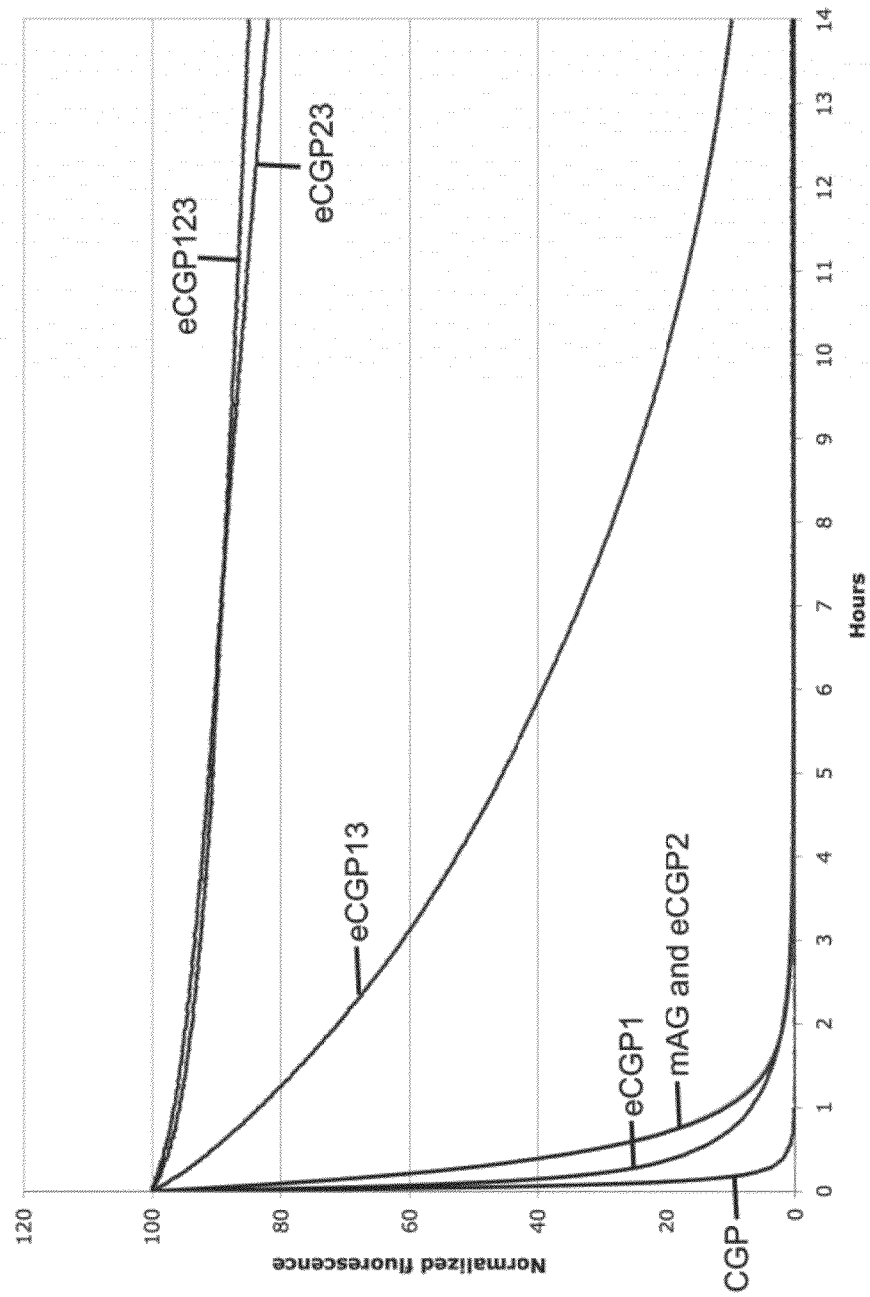

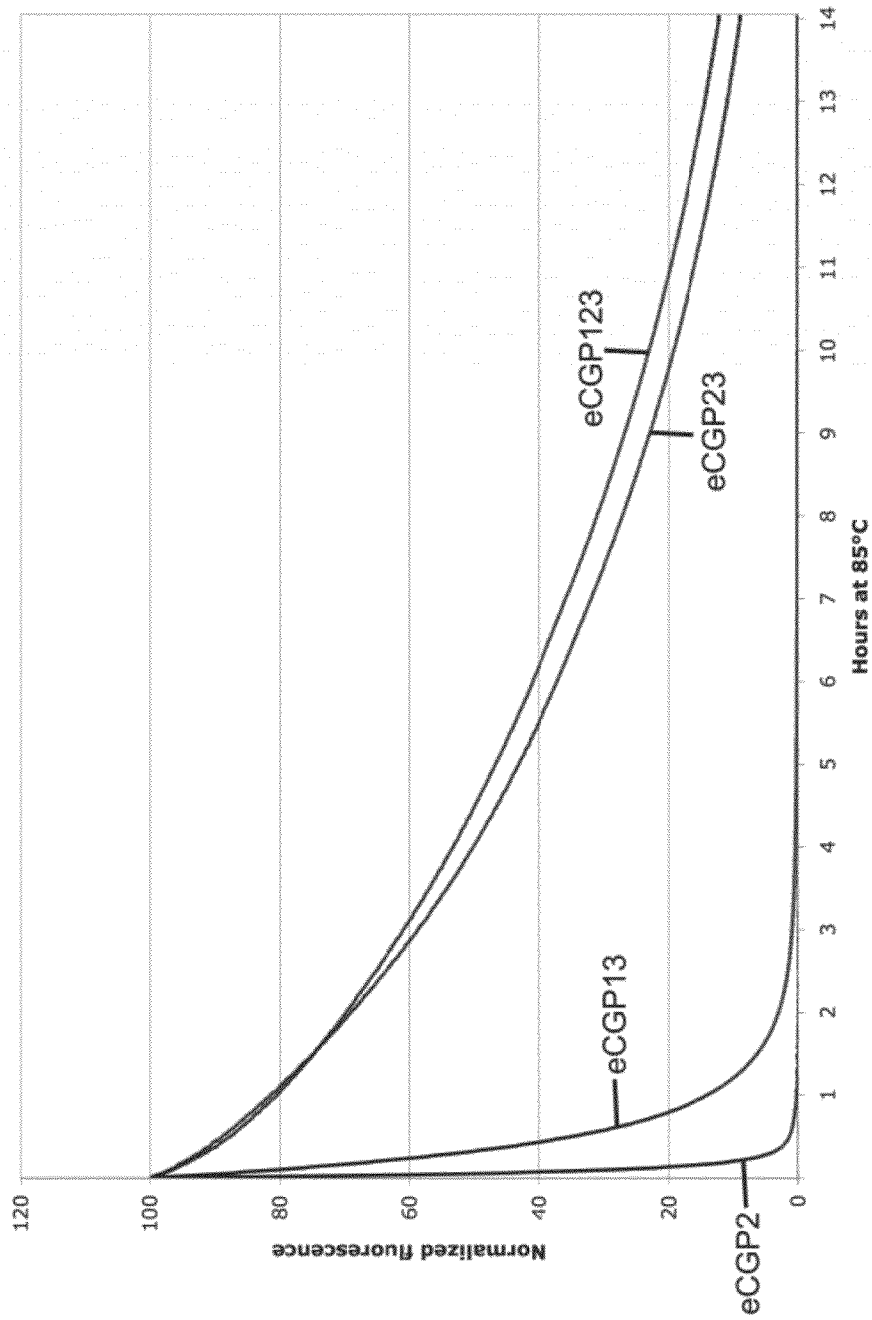

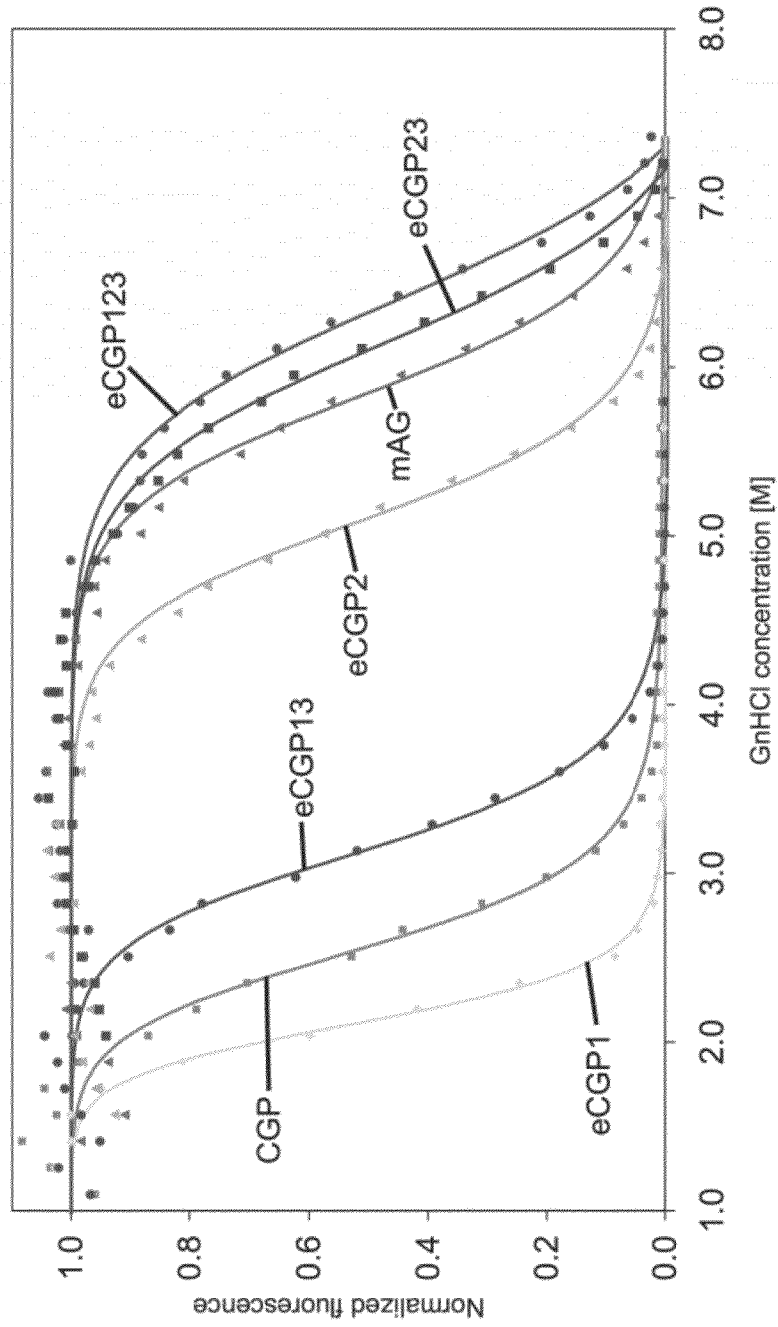

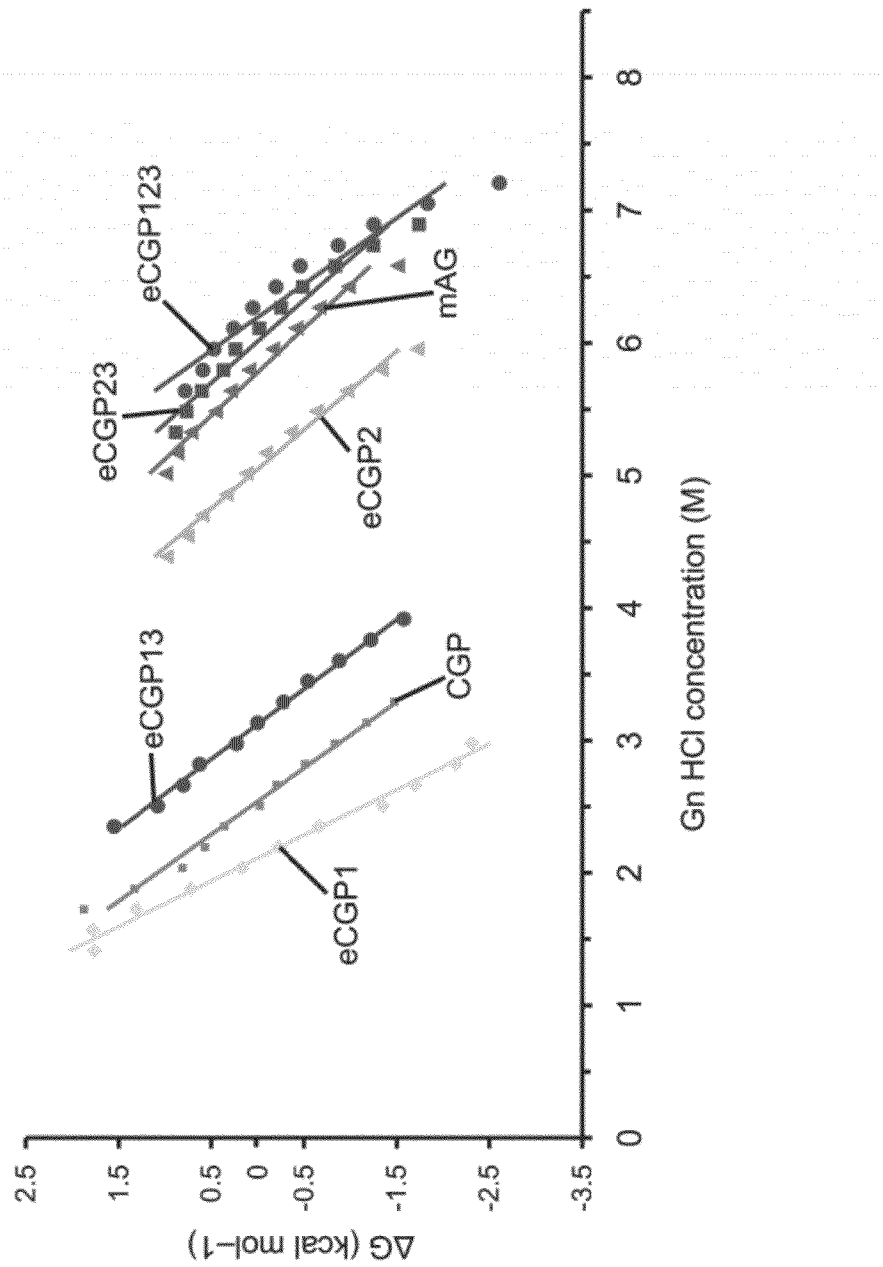
Figure 6B: Dependence of the standard free energy of denaturation on guanidine concentration

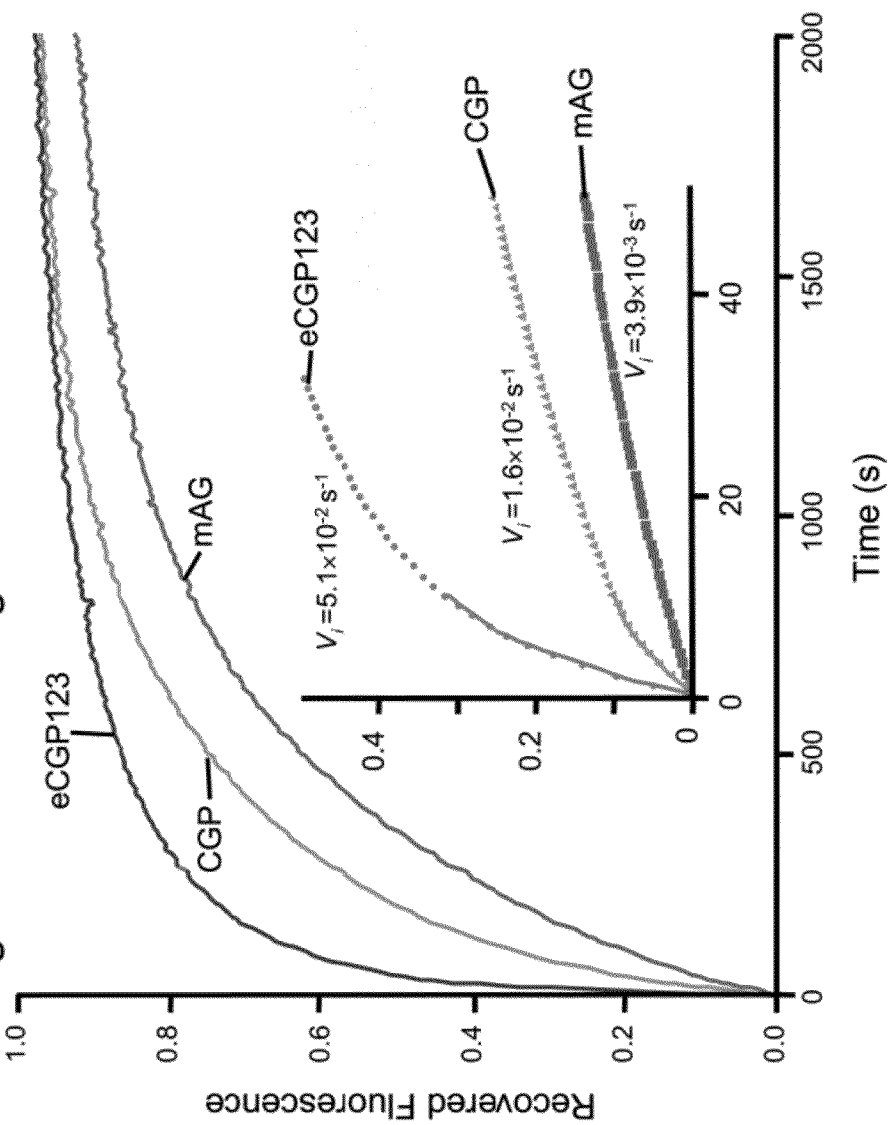

SEQUENCE LISTING

```
<160> NUMBER OF SEQ ID NOS: 27

<210> SEQ ID NO 1
<211> LENGTH: 681
<212> TYPE: DNA
<213> ORGANISM: Artificial
<220> FEATURE:
<223> OTHER INFORMATION: Synthetic DNA encoding engineered fluorescent
      protein

<400> SEQUENCE: 1
atgtcagtaa ttaaaccgga aatgaaaatt aaattgcgta tggaaggtgc cgttaacggc      60
cataaatttg taattgaagg ggaaggaaaa ggcaacccat tcgaaggaac ccagaccctg     120
gatttaaccg taaaagaagg cgcacctctc cctttcgcgt acgacatcct caccccagtc     180
ttccaatacg gcaatcgcgc tttcgccaaa tacccacaag atattccaga ctattttaaa     240
caaacattcc ccgaaggcta ttcttgggaa cgctctatga cctatgaaga tcatggaatt     300
tgtatcgcta cctccgacat tactatggaa ggcgactgtt ttatttataa aattcgcttt     360
gatggaacta acttcccccc gaacggccct gtaatgcaaa agaagacctt aaaatgggaa     420
cctagcaccg aaaaaatgta tgtacgcgac ggagttctta agggtgacgt aaacatggca     480
cttctgctcg aaggaggtgg acactaccgc tgcgattta aaaccactta taaagccaaa     540
aaagatgttc gtcttccaga tgcacacaag gtggaccacc gcattgaaat cctgagccac     600
gataaagatt ataataaagt taaactctat gaacacgccg aagcccgcta ttctatgtta     660
ccgtctcagg ctaaagctag c                                               681

<210> SEQ ID NO 2
<211> LENGTH: 681
<212> TYPE: DNA
<213> ORGANISM: Artificial
<220> FEATURE:
<223> OTHER INFORMATION: Synthetic DNA encoding engineered fluorescent
      protein

<400> SEQUENCE: 2
atgtcagtaa ttaaaccgga aatgaaaatt aaattgcgtt tggaaggtgc cgttaacggc      60
catgaatttg taattgaagg agaaggaaaa ggcaaaccat tcgaaggaac ccagaccctg     120
gatttaaccg taaaagaagg cgcacctctc cctttcgcgt acgacatcct caccccagcc     180
ttccaatacg gcaatcgcgc tttcgccaaa tacccaaaag atattccaga ctattttaaa     240
caaacattcc ccgaaggcta ttcttgggaa cgctctatga cctatgaaga tcaaggaatt     300
```

```
tgtatcgcta cctccgacat tactatggaa ggagactgtt ttttttataa aattcgcttt    360
gatggaacta acttcccccc gaacggccct gtaatgcaaa agaagacctt aaaatgggaa    420
cctagcaccg aaaaaatgta tgtacgcgac ggagttctta agggtgacgt aaacatggca    480
cttctgctcg aaggaggtgg acactaccgc tgcgatttta aaaccactta taaagccaaa    540
aaagatgttc gtcttccaga tgcacacaag gtggaccacc gcattgaaat cctgagccac    600
gataaagatt ataataaagt taaactctat gaacacgccg aagcccgcta ttctatgtta    660
ccgtctcagg ctaaagctag c                                              681
```

<210> SEQ ID NO 3
<211> LENGTH: 681
<212> TYPE: DNA
<213> ORGANISM: Artificial
<220> FEATURE:
<223> OTHER INFORMATION: Synthetic DNA encoding engineered fluorescent
      protein

<400> SEQUENCE: 3

```
atgtcagtaa ttaaaccgga aatgaaaatt aaattgcgta tggaaggtgc cgttaacggc     60
cataaatttg taattgaagg ggaaggaaaa ggcaacccat tcgaaggaac ccagaccctg    120
gatttaaccg taaggaagg cgcacctctc cctttcgcgt acgacatcct caccccagtc    180
ttccaatacg gcaatcgcgc tttcaccaaa tacccacaag atattccaga ctattttaaa    240
caaacattcc ccgaaggcta ttcttgggaa cgctctatga cctatgaaga tcatggaatt    300
tgtatcgcta cctccgacat tactatggaa ggcgactgtt ttatttataa aattcgcttt    360
gatggaacta acttcccccc aaacggccct gtaatgcaaa agaagacctt aaaatgggaa    420
cctagcaccg aaaaaatgta tgtacgcgac ggagttctta agggtgacgt aaacatggca    480
cttctgctcg aaggaggtgg acactaccgc tgcgatttta aaaccactta taaagccaaa    540
aaagatgttc gtcttccagg tgcacacaag gtggaccacc gcattgaaat cctgagccac    600
gataaagatt ataataaagt taaactctat gaacacgccg aagcccgcta ttctatgtta    660
ccgtctcagg ctaaagctag c                                              681
```

<210> SEQ ID NO 4
<211> LENGTH: 681
<212> TYPE: DNA
<213> ORGANISM: Artificial
<220> FEATURE:
<223> OTHER INFORMATION: Synthetic DNA encoding engineered fluorescent
      protein

<400> SEQUENCE: 4

```
atgtcagtaa ttaaaccgga aatgaaaatt aaattgcgtt tggaaggtgc cgttaacggc     60
catgaatttg taattgaagg agaaggaaaa ggcaaaccat tcgaaggaac ccagaccctg    120
gatttaaccg taaagaagg cgcacctctc cctttcgcgt acgacatcct caccccagcc    180
ttccaatacg gcaatcgcgc tttcaccaaa tacccaaaag atattccaga ctattttaaa    240
caaacattcc ccgaaggcta ttcttgggaa cgctctatga cctatgaaga tcaaggaatt    300
tgtatcgcta cctccgacat tactatggaa ggagactgtt ttttttataa gattcgcttt    360
gatggaacta acttcccccc gaacggccct gtaatgcaaa agaagacctt aaaatgggaa    420
cctagcaccg aaaaaatgta tgtacgcgac ggagttctta agggtgacgt aaacatggca    480
cttctgctcg aaggaggtgg acactaccgc tgcgatttta aaaccactta taaagccaaa    540
aaagatgttc gtcttccaga tgcacacgag gtggaccacc gcattgaaat cctgagccac    600
```

```
gataaagatt ataataaagt taaactctat gaacacgccg aagcccgcta ttctatgtta    660
ccgtctcagg ctaaagctag c                                              681
```

<210> SEQ ID NO 5
<211> LENGTH: 681
<212> TYPE: DNA
<213> ORGANISM: Artificial
<220> FEATURE:
<223> OTHER INFORMATION: Synthetic DNA encoding engineered fluorescent
      protein

<400> SEQUENCE: 5

```
atgtcagtaa ttaaaccgga atgaaaatt aaattgcgta tggaaggtgc cgttaacggc    60
cataaatttg taattgaagg agaaggaata ggcaaaccat acgaaggaac ccagaccctg   120
gatttaaccg taaagaagg cgcacctctc cctttctcgt acgacatcct caccccagcc   180
ttccaatacg gcaatcgcgc tttcaccaaa tacccaaaag atattccaga ctatttaaa   240 caagcattcc ccgaaggcta tcttgggaa cgctctatga cctatgaaga tcaaggaatt   300
tgtatcgcta cctccgacat tactatgaa ggagactgtt ttttttataa gattcgcttt   360
gatggaacta acttccccc gaacggccct gtaatgcaaa agaagacctt aaaatgggaa   420
cctagcaccg aaaaaatgta tgtacgcgac ggagttctta agggtgacgt aaacatggca   480
cttctgctcg aaggaggtgg acactaccgc tgcgatttta aaccacttaa aagccaaa    540 aaagatgttc gtcttccaga tgcacacgag gtggaccacc gcattgaaat cctgagccac   600
gataaagatt ataataaagt tagactctat gaacacgccg aagcccgcta ttctatgtta   660
ccgtctcagg ctaaagctag c                                              681
```

<210> SEQ ID NO 6
<211> LENGTH: 225
<212> TYPE: PRT
<213> ORGANISM: Artificial
<220> FEATURE:
<223> OTHER INFORMATION: Synthetic fluorescent protein

<400> SEQUENCE: 6

```
Met Ser Val Ile Lys Pro Glu Met Lys Ile Lys Leu Arg Met Glu Gly
 1               5                  10                  15

Ala Val Asn Gly His Lys Phe Val Ile Glu Gly Glu Gly Gly Gly Asn
                20                  25                  30

Pro Phe Glu Gly Thr Gln Thr Leu Asp Leu Thr Val Lys Glu Gly Ala
            35                  40                  45

Pro Leu Pro Phe Ala Tyr Asp Ile Leu Thr Pro Val Phe Gln Tyr Gly
        50                  55                  60

Asn Arg Ala Phe Ala Lys Tyr Pro Gln Asp Ile Pro Asp Tyr Phe Lys
65                  70                  75                  80

Gln Thr Phe Pro Glu Gly Tyr Ser Trp Glu Arg Ser Met Thr Tyr Glu
                85                  90                  95

Asp His Gly Ile Cys Ile Ala Thr Ser Asp Ile Thr Met Glu Gly Asp
            100                 105                 110

Cys Phe Ile Tyr Lys Ile Arg Phe Asp Gly Thr Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160
```

```
Leu Leu Leu Glu Gly Gly Gly His Tyr Arg Cys Asp Phe Lys Thr Thr
            165                 170                 175

Tyr Lys Ala Lys Lys Asp Val Arg Leu Pro Asp Ala His Lys Val Asp
            180                 185                 190

His Arg Ile Glu Ile Leu Ser His Asp Lys Asp Tyr Asn Lys Val Lys
            195                 200                 205

Leu Tyr Glu His Ala Glu Ala Arg Tyr Ser Met Leu Pro Ser Gln Ala
            210                 215                 220

Lys
225

<210> SEQ ID NO 7
<211> LENGTH: 225
<212> TYPE: PRT
<213> ORGANISM: Artificial
<220> FEATURE:
<223> OTHER INFORMATION: Synthetic fluorescent protein

<400> SEQUENCE: 7

Met Ser Val Ile Lys Pro Glu Met Lys Ile Lys Leu Arg Leu Glu Gly
1               5                   10                  15

Ala Val Asn Gly His Glu Phe Val Ile Glu Gly Glu Gly Lys Gly Lys
            20                  25                  30

Pro Phe Glu Gly Thr Gln Thr Leu Asp Leu Thr Val Lys Glu Gly Ala
            35                  40                  45

Pro Leu Pro Phe Ala Tyr Asp Ile Leu Thr Pro Ala Phe Gln Tyr Gly
        50                  55                  60

Asn Arg Ala Phe Ala Lys Tyr Pro Lys Asp Ile Pro Asp Tyr Phe Lys
65                  70                  75                  80

Gln Thr Phe Pro Glu Gly Tyr Ser Trp Glu Arg Ser Met Thr Tyr Glu
                85                  90                  95

Asp Gln Gly Ile Cys Ile Ala Thr Ser Asp Ile Thr Met Glu Gly Asp
            100                 105                 110

Cys Phe Phe Tyr Lys Ile Arg Phe Asp Gly Thr Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
            165                 170                 175

Tyr Lys Ala Lys Lys Asp Val Arg Leu Pro Asp Ala His Lys Val Asp
            180                 185                 190

His Arg Ile Glu Ile Leu Ser His Asp Lys Asp Tyr Asn Lys Val Lys
            195                 200                 205

Leu Tyr Glu His Ala Glu Ala Arg Tyr Ser Met Leu Pro Ser Gln Ala
            210                 215                 220

Lys
225

<210> SEQ ID NO 8
<211> LENGTH: 225
<212> TYPE: PRT
<213> ORGANISM: Artificial
<220> FEATURE:
<223> OTHER INFORMATION: Synthetic fluorescent protein

<400> SEQUENCE: 8
```

```
Met Ser Val Ile Lys Pro Glu Met Lys Ile Lys Leu Arg Met Glu Gly
1               5                   10                  15
Ala Val Asn Gly His Lys Phe Val Ile Glu Gly Glu Gly Lys Gly Asn
                20                  25                  30
Pro Phe Glu Gly Thr Gln Thr Leu Asp Leu Thr Val Lys Glu Gly Ala
            35                  40                  45
Pro Leu Pro Phe Ala Tyr Asp Ile Leu Thr Pro Val Phe Gln Tyr Gly
    50                  55                  60
Asn Arg Ala Phe Thr Lys Tyr Pro Gln Asp Ile Pro Asp Tyr Phe Lys
65                  70                  75                  80
Gln Thr Phe Pro Glu Gly Tyr Ser Trp Glu Arg Ser Met Thr Tyr Glu
                85                  90                  95
Asp His Gly Ile Cys Ile Ala Thr Ser Asp Ile Thr Met Glu Gly Asp
            100                 105                 110
Cys Phe Ile Tyr Lys Ile Arg Phe Asp Gly Thr Asn Phe Pro Pro Asn
    115                 120                 125
Gly Pro Val Met Gln Lys Lys Thr Leu Lys Trp Glu Pro Ser Thr Glu
    130                 135                 140
Lys Met Tyr Val Arg Asp Gly Val Leu Lys Gly Asp Val Asn Met Ala
145                 150                 155                 160
Leu Leu Leu Glu Gly Gly Gly His Tyr Arg Cys Asp Phe Lys Thr Thr
                165                 170                 175
Tyr Lys Ala Lys Lys Asp Val Arg Leu Pro Gly Ala His Lys Val Asp
            180                 185                 190
His Arg Ile Glu Ile Leu Ser His Asp Lys Asp Tyr Asn Lys Val Lys
            195                 200                 205
Leu Tyr Glu His Ala Glu Ala Arg Tyr Ser Met Leu Pro Ser Gln Ala
    210                 215                 220
Lys
225

<210> SEQ ID NO 9
<211> LENGTH: 225
<212> TYPE: PRT
<213> ORGANISM: Artificial
<220> FEATURE:
<223> OTHER INFORMATION: Synthetic fluorescent protein

<400> SEQUENCE: 9

Met Ser Val Ile Lys Pro Glu Met Lys Ile Lys Leu Arg Leu Glu Gly
1               5                   10                  15
Ala Val Asn Gly His Glu Phe Val Ile Glu Gly Glu Gly Lys Gly Lys
                20                  25                  30
Pro Phe Glu Gly Thr Gln Thr Leu Asp Leu Thr Val Lys Glu Gly Ala
            35                  40                  45
Pro Leu Pro Phe Ala Tyr Asp Ile Leu Thr Pro Ala Phe Gln Tyr Gly
    50                  55                  60
Asn Arg Ala Phe Thr Lys Tyr Pro Lys Asp Ile Pro Asp Tyr Phe Lys
65                  70                  75                  80
Gln Thr Phe Pro Glu Gly Tyr Ser Trp Glu Arg Ser Met Thr Tyr Glu
                85                  90                  95
Asp Gln Gly Ile Cys Ile Ala Thr Ser Asp Ile Thr Met Glu Gly Asp
            100                 105                 110
Cys Phe Phe Tyr Lys Ile Arg Phe Asp Gly Thr Asn Phe Pro Pro Asn
    115                 120                 125
Gly Pro Val Met Gln Lys Lys Thr Leu Lys Trp Glu Pro Ser Thr Glu
```

```
                130                 135                 140
Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                165                 170                 175

Tyr Lys Ala Lys Lys Asp Val Arg Leu Pro Asp Ala His Glu Val Asp
                180                 185                 190

His Arg Ile Glu Ile Leu Ser His Asp Lys Asp Tyr Asn Lys Val Lys
                195                 200                 205

Leu Tyr Glu His Ala Glu Ala Arg Tyr Ser Met Leu Pro Ser Gln Ala
                210                 215                 220

Lys
225

<210> SEQ ID NO 10
<211> LENGTH: 225
<212> TYPE: PRT
<213> ORGANISM: Artificial
<220> FEATURE:
<223> OTHER INFORMATION: Synthetic fluorescent protein

<400> SEQUENCE: 10

Met Ser Val Ile Lys Pro Glu Met Lys Ile Lys Leu Arg Met Glu Gly
1               5                   10                  15

Ala Val Asn Gly His Lys Phe Val Ile Glu Gly Glu Gly Ile Gly Lys
                20                  25                  30

Pro Tyr Glu Gly Thr Gln Thr Leu Asp Leu Thr Val Lys Glu Gly Ala
                35                  40                  45

Pro Leu Pro Phe Ser Tyr Asp Ile Leu Thr Pro Ala Phe Gln Tyr Gly
                50                  55                  60

Asn Arg Ala Phe Thr Lys Tyr Pro Lys Asp Ile Pro Asp Tyr Phe Lys
65                  70                  75                  80

Gln Ala Phe Pro Glu Gly Tyr Ser Trp Glu Arg Ser Met Thr Tyr Glu
                85                  90                  95

Asp Gln Gly Ile Cys Ile Ala Thr Ser Asp Ile Thr Met Glu Gly Asp
                100                 105                 110

Cys Phe Phe Tyr Lys Ile Arg Phe Asp Gly Thr Asn Phe Pro Pro Asn
                115                 120                 125

Gly Pro Val Met Gln Lys Lys Thr Leu Lys Trp Glu Pro Ser Thr Glu
                130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                165                 170                 175

Tyr Lys Ala Lys Lys Asp Val Arg Leu Pro Asp Ala His Glu Val Asp
                180                 185                 190

His Arg Ile Glu Ile Leu Ser His Asp Lys Asp Tyr Asn Lys Val Arg
                195                 200                 205

Leu Tyr Glu His Ala Glu Ala Arg Tyr Ser Met Leu Pro Ser Gln Ala
                210                 215                 220

Lys
225

<210> SEQ ID NO 11
<211> LENGTH: 43
<212> TYPE: DNA
<213> ORGANISM: Artificial
```

```
<220> FEATURE:
<223> OTHER INFORMATION: Synthetic amplification primer

<400> SEQUENCE: 11
cttgcaatcc gatcttgcag caggtgactt cgactcttgg ggt            43

<210> SEQ ID NO 12
<211> LENGTH: 65
<212> TYPE: DNA
<213> ORGANISM: Artificial
<220> FEATURE:
<223> OTHER INFORMATION: Synthetic amplificaiton primer

<400> SEQUENCE: 12
cttgcaatcc gatcttgcag caggtgactt cgactcttgg ggtaacggcc ataaatttgt    60
aattg                                                               65

<210> SEQ ID NO 13
<211> LENGTH: 43
<212> TYPE: DNA
<213> ORGANISM: Artificial
<220> FEATURE:
<223> OTHER INFORMATION: Synthetic amplification primer

<400> SEQUENCE: 13
cacctgctgc aagatcggat tgcaagtaga agctacgagc act            43

<210> SEQ ID NO 14
<211> LENGTH: 62
<212> TYPE: DNA
<213> ORGANISM: Artificial
<220> FEATURE:
<223> OTHER INFORMATION: Synthetic amplification primer

<400> SEQUENCE: 14
cacctgctgc aagatcggat tgcaagtaga agctacgagc actaacggca ccttccatac    60
gc                                                                  62

<210> SEQ ID NO 15
<211> LENGTH: 43
<212> TYPE: DNA
<213> ORGANISM: Artificial
<220> FEATURE:
<223> OTHER INFORMATION: Synthetic amplification primer

<400> SEQUENCE: 15
cctccaaagt gacttagctg ccggcgattt tgatagctgg ggc            43

<210> SEQ ID NO 16
<211> LENGTH: 63
<212> TYPE: DNA
<213> ORGANISM: Artificial
<220> FEATURE:
<223> OTHER INFORMATION: Synthetic amplification primer

<400> SEQUENCE: 16
cctccaaagt gacttagctg ccggcgattt tgatagctgg ggcgatcaag gaatttgtat    60
cgc                                                                 63

<210> SEQ ID NO 17
<211> LENGTH: 43
<212> TYPE: DNA
<213> ORGANISM: Artificial
<220> FEATURE:
<223> OTHER INFORMATION: Synthetic amplification primer
```

```
<400> SEQUENCE: 17
cgccggcagc taagtcactt tggaggtaaa atgagcgggc cga                43

<210> SEQ ID NO 18
<211> LENGTH: 64
<212> TYPE: DNA
<213> ORGANISM: Artificial
<220> FEATURE:
<223> OTHER INFORMATION: Synthetic amplification primer

<400> SEQUENCE: 18
cgccggcagc taagtcactt tggaggtaaa atgagcgggc cgattcatag gtcatagagc    60
gttc                                                                 64

<210> SEQ ID NO 19
<211> LENGTH: 43
<212> TYPE: DNA
<213> ORGANISM: Artificial
<220> FEATURE:
<223> OTHER INFORMATION: Synthetic amplification primer

<400> SEQUENCE: 19
tttacagtct gacttggcgg ctggggattt cgattcgtgg ggg                43

<210> SEQ ID NO 20
<211> LENGTH: 63
<212> TYPE: DNA
<213> ORGANISM: Artificial
<220> FEATURE:
<223> OTHER INFORMATION: Synthetic amplification primer

<400> SEQUENCE: 20
tttacagtct gacttggcgg ctggggattt cgattcgtgg ggggaggtg gacactaccg     60 ctg                                                                  63

<210> SEQ ID NO 21
<211> LENGTH: 43
<212> TYPE: DNA
<213> ORGANISM: Artificial
<220> FEATURE:
<223> OTHER INFORMATION: Synthetic amplification primer

<400> SEQUENCE: 21
ccccagccgc caagtcagac tgtaaataga aagaccgcgc aga                43

<210> SEQ ID NO 22
<211> LENGTH: 62
<212> TYPE: DNA
<213> ORGANISM: Artificial
<220> FEATURE:
<223> OTHER INFORMATION: Synthetic amplification primer

<400> SEQUENCE: 22
ccccagccgc caagtcagac tgtaaataga aagaccgcgc agattcgagc agaagtgcca    60
tg                                                                   62

<210> SEQ ID NO 23
<211> LENGTH: 41
<212> TYPE: DNA
<213> ORGANISM: Artificial
<220> FEATURE:
<223> OTHER INFORMATION: Synthetic amplification primer

<400> SEQUENCE: 23
```

```
tttgccgcta gctttagcct gagacggtaa catagaatag c                    41
```

<210> SEQ ID NO 24
<211> LENGTH: 35
<212> TYPE: DNA
<213> ORGANISM: Artificial
<220> FEATURE:
<223> OTHER INFORMATION: Synthetic amplification primer

<400> SEQUENCE: 24

```
tacatatggg cgcgcatgcc tcagtaatta aaccg                           35
```

<210> SEQ ID NO 25
<211> LENGTH: 20
<212> TYPE: PRT
<213> ORGANISM: Artificial
<220> FEATURE:
<223> OTHER INFORMATION: Synthetic peptide

<400> SEQUENCE: 25

```
Ser Ala Arg Ser Phe Tyr Leu Gln Ser Asp Leu Ala Ala Gly Asp Phe
1               5                  10                  15

Asp Ser Trp Gly
            20
```

<210> SEQ ID NO 26
<211> LENGTH: 20
<212> TYPE: PRT
<213> ORGANISM: Artificial
<220> FEATURE:
<223> OTHER INFORMATION: Synthetic Peptide

<400> SEQUENCE: 26

```
Ser Ala Arg Ser Phe Tyr Leu Gln Ser Asp Leu Ala Ala Gly Asp Phe
1               5                  10                  15

Asp Ser Trp Gly
            20
```

<210> SEQ ID NO 27
<211> LENGTH: 225
<212> TYPE: PRT
<213> ORGANISM: Artificial
<220> FEATURE:
<223> OTHER INFORMATION: Synthetic Fluorescent Protein

<400> SEQUENCE: 27

```
Met Ser Val Ile Lys Pro Asp Met Lys Ile Lys Leu Arg Met Glu Gly
1               5                  10                  15

Ala Val Asn Gly His Lys Phe Val Ile Glu Gly Glu Gly Lys Gly Lys
            20                  25                  30

Pro Phe Glu Gly Thr Gln Thr Met Asp Leu Thr Val Lys Glu Gly Ala
        35                  40                  45

Pro Leu Pro Phe Ala Tyr Asp Ile Leu Thr Thr Val Phe Gln Tyr Gly
    50                  55                  60

Asn Arg Ala Phe Ala Lys Tyr Pro Lys Asp Ile Pro Asp Tyr Phe Lys
65                  70                  75                  80

Gln Thr Phe Pro Glu Gly Tyr Ser Trp Glu Arg Ser Met Thr Tyr Glu
                85                  90                  95

Asp Gln Gly Ile Cys Ile Ala Thr Ser Asp Ile Thr Met Glu Gly Asp
            100                 105                 110

Cys Phe Phe Tyr Lys Asp Gly Thr Asn Phe Pro Pro Asn Gly Pro Val
        115                 120                 125
```

```
Met Gln Lys Lys Thr Leu Lys Trp Glu Pro Ser Thr Glu Lys Met Tyr
        130                 135                 140

Val Arg Asp Gly Val Leu Lys Gly Asp Val Asn Met Ala Leu Leu Leu
145                 150                 155                 160

Glu Gly Gly Gly His Tyr Arg Cys Asp Phe Lys Thr Thr Tyr Lys Ala
                165                 170                 175

Lys Lys Asp Val Arg Leu Pro Asp Ala His Lys Val Asp His Arg Ile
            180                 185                 190

Glu Ile Leu Ser His Asp Lys Asp Tyr Asn Lys Val Lys Leu Tyr Glu
        195                 200                 205

His Ala Glu Ala Arg Tyr Ser Met Leu Pro Ser Gln Ala Lys Ile Arg
        210                 215                 220

Phe
225
```

HIGHLY THERMOSTABLE FLUORESCENT PROTEINS

RELATED APPLICATIONS

This patent application is a divisional of patent application Ser. No. 13/023,421 filed Feb. 8, 2011, which is a divisional of patent application Ser. No. 12/317,185 filed Dec. 19, 2008, and claims the benefit of the filing date of U.S. Provisional Patent Application No. 61/008,689 filed Dec. 21, 2007.

STATEMENT AS TO RIGHTS TO INVENTIONS MADE UNDER FEDERALLY SPONSORED RESEARCH OR DEVELOPMENT

This invention was made with government support under Contract No. DE-AC52-06 NA 25396 awarded by the U.S. Department of Energy. The government has certain rights in the invention.

BACKGROUND OF THE INVENTION

GFP and its numerous related fluorescent proteins are now in widespread use as protein tagging agents (for review, see Verkhusha et al., 2003, *GFP-like fluorescent proteins and chromoproteins of the class Anthozoa*. In: Protein Structures: Kaleidescope of Structural Properties and Functions, Ch. 18, pp. 405-439, Research Signpost, Kerala, India). GFP-like proteins are an expanding family of homologous, 25-30 kDa polypeptides sharing a conserved 11 beta-strand "barrel" structure. The GFP-like protein family currently comprises well over 100 members, cloned from various *Anthozoa* and *Hydrozoa* species, and includes red, yellow and green fluorescent proteins and a variety of non-fluorescent chromoproteins. A wide variety of fluorescent protein labeling assays and kits are commercially available, encompassing a broad spectrum of GFP spectral variants and GFP-like fluorescent proteins, including DsRed and other red fluorescent proteins (Clontech, Palo Alto, Calif.; Amersham, Piscataway, N.J.).

However, the stability of fluorescent proteins is limited. Various approaches aimed at stabilizing fluorescent proteins have been undertaken. For example, Siemering et al. described the generation of a GFP mutant (GFPA) using site-directed mutagenesis, reporting that the mutant showed reduced sensitivity to temperature in both bacteria and yeast cultured at 37° C. (Siemering et al., 1996, Curr Biol 6: 1653). U.S. Pat. No. 6,414,119 described a GFP mutant showing modest improvements in thermal stability over wild type GFP (reportedly retaining fluorescence and solubility at 42° C., and showing some fluorescence at 50° C.). More recently, Pedelacq et al.,[7] used directed evolution to increase the stability of GFP by selecting for resistance to the destabilizing effects of a poorly folding and aggregating ferritin sequence fused upstream. The first fusions were very weakly fluorescent, but with further evolution of the GFP, this external destabilization could be overcome and a variant (termed "superfolder GFP") able to resist the folding interference of ferritin was selected. This was shown to be considerably more stable than standard GFP by a number of different measures, including resistance to thermal and chemical denaturation.

A number of different methods have been developed to create thermostable proteins, most of which involve the creation of libraries and the identification of improved proteins by selection or screening. Conceptually, the most straightforward way to identify proteins with improved thermostability has been to apply a thermal challenge to a collection of individual clones and test the remaining functionality of the clones, repeating this process if necessary, to combine useful mutations[8-10]. A similar method, which does not rely on such extensive screening requirements, involves direct selection of clones growing at elevated temperature within thermophilic bacteria. However, to date, this method has only been applied to the selection of thermophilic antibiotic resistance proteins[11, 12], and as laboratory organisms typically do not grow at elevated temperatures, it has been difficult to generalize. As a result, considerable effort has been put into the development of alternative approaches which involve selection or screening for biophysical or biological properties which can serve as surrogates for, and are often correlated with, thermostability.

One of the first examples of this approach is the PROSIDE (protein stability increased by directed evolution)[13-20] approach in which resistance to protease digestion is used as the surrogate property for protein stability, with filamentous phage infectivity being the selection modality. Proteins under test are expressed between two domains in g3p (the phage receptor for bacteria): if they are cleaved by protease, the filamentous phage loses the N terminal g3p domain and consequently its ability to infect: if the protein is protease resistant infectivity is maintained. This has been successfully used to increase the stability of the beta1 domain of protein G[15], the cold shock protein of *B. subtilis*[17] and ribonuclease T1[13]. In another approach involving directed evolution, Shusta et al., showed that the display levels of heterologous proteins on the surface of yeast correlated with expression levels and thermal stability[21], although exceptions to this have been recently described[22].

Consensus engineering[23, 24] is an approach to increase protein stability which does not use directed evolution, but the informational content of aligned sequences. By modifying a sequence so that it more closely resembles a consensus derived from the alignment of numerous proteins of a particular family, it has been found that significant increases in stability can be obtained. This has been applied to antibodies and antibody fragments[5, 24-31], GroEL minichaperones[32, 33], p53[34], WW[35] and SH3 domains[36]. More recently consensus engineering, has been applied to the creation of novel proteins, rather than the stepwise modification of pre-existing ones to resemble a consensus. Perhaps the most striking success was the application to phytases[37-40], in which a final protein with a Tm of 90.4° C. was obtained: 52° C. greater than the best component parental sequence[40]. Similar stability was obtained with a consensus ankyrin sequence based on the alignment of 2000 different ankyrins[41-43]. We recently applied this method to the creation of a consensus green protein (CGP)[44].

Although we obtained a functional fluorescent protein, its Tm was 5° C. less than the monomeric Azami Green[45] used to identify the sequences comprising the consensus. However, in this case no effort was made to examine the effects of individual mutations, and it is likely that some of the consensus mutations were destabilizing, as had been previously shown for the phytase[37-40].

Other methods used to increase protein stability, relying heavily on structural information, include "helix capping"[46-49] or optimization[50-52], the introduction of salt bridges or their replacement by hydrophobic interactions[53-59], the introduction of clusters of aromatic-aromatic interactions[60-62] and rigidification strategies, in which disulfide bonds or glycine to alanine, or Xaa to proline changes are introduced[63-65]. However, most of these have been carried out on model structures, and none has been widely adopted.

Thermostabilization of proteins is regarded as important in a number of biotechnological and pharmaceutical applications. Within the context of industrial enzymes, thermostability leads to longer enzyme survival times, as well as more efficient reactions at higher temperatures and diminished microbial contamination, all of which result in diminished costs, while in the pharmaceutical arena, thermostability of protein therapeutics leads to longer half lives and more effective drugs[1-3]. Thermostability has also been regarded as important in the use of proteins as scaffolds to generate libraries of specific binders. It has been reasoned that if a starting scaffold is more stable, it will be more tolerant to the destabilizing effects of mutations, or insertions, used to mediate binding. This has been shown for affinity reagents based on ankyrins[4], and has also been applied to the creation of phage antibody libraries[5]. Finally, proteins of increased thermostability are more resistant to mutations than the protein from which they are derived, promoting evolvability by providing greater permissivity to mutations leading to novel functions[6, 7].

SUMMARY OF THE INVENTION

The invention relates novel and highly thermostable fluorescent proteins (TSFPs), methods for generating these and other stability-enhanced proteins, polynucleotides encoding such proteins, and assays and method for using the TSFPs and TSFP-encoding nucleic acid molecules of the invention. Exemplary TSFPs are provided. In particular, polypeptides comprising eCGPs of the invention, including but not limited to those having the sequences of SEQ ID NOS: 9 and 10, are provided. Additionally, nucleic acid molecules comprising a polynucleotide encoding such polypeptides are also provided, and include without limitation, nucleic acid molecules which comprise polynucleotides encoding the sequences of SEQ ID NOS: 4 and 5. Vectors comprising such nucleic acid molecules are also provided, as are cells comprising such vectors.

The invention also provides a method for generating stability-enhanced variants of a protein, including but not limited to fluorescent proteins. The method of the invention is described, infra, and in the Examples which follow. Briefly, in a simplified description, the method entails internally destabilizing the protein using a heterologous insertion, evolving the protein sequences adjacent to the heterologous insertion to overcome the destabilization, and then removing the heterologous insert.

The TSFPs of the invention show extremely enhanced levels of stability and thermotolerance. In one case, for example, a TSFP of the invention is so stable it can be heated to 99° C. for short periods of time without denaturing, and retains 85% of its fluorescence when heated to 80° C. for several minutes.

BRIEF DESCRIPTION OF THE DRAWINGS

FIG. 1. Schematic outline of the internal destabilization methodology used to generate thermostable variants of CGP, an artificial fluorescent protein (Dai et al., 2007, supra). (A) strategy applied to CGP. After the insertion of a single insert, CGP loses fluorescence which was regained by mutation and selection. This process was repeated until fluorescent proteins resistant to the destabilizing effects of three loops were obtained. For each evolved fluorescent variant, a gene is synthesized which lacks the inserted loop(s). (B) shows induced bacterial colonies, with a colony expressing CGP before (colony 1) and after insertion of the HCDR3 in loop 1 (colony 2) or loop 2 (colony 3). The remaining colonies are mutated variants, showing the improvement in fluorescence.

FIG. 2. Accumulation of amino acid mutations through iterative internal destabilization. The original sequence of CGP is represented by the small squares at the top, with the positions of amino acids that underwent mutation indicated as black boxes. The exact positions and wild type sequences of these are shown below, with the three insertion sites indicated as inverted red triangles flanked by the exact positions. The mutations occurring at each site, for each evolutionary round and loop insertion strategy, are shown. White squares indicate wild type sequence. Where a mutation has occurred, the letter indicates the new mutation, and the number the percentage of the sequenced fluorescent clones that contain that mutation. This is also represented graphically by that portion of the white square colored green. For example, at position 7, in all early evolutionary rounds 100% of clones changed the wild type aspartate to a glutamate. If more than one mutation is found at a particular site, both amino acids are given with their percentages, indicated by green and yellow boxes. After three rounds when loops 2 and 3 were targeted, 12% of clones also showed a valine at this position, which increased to 50% in later rounds. The percentage of clones carrying a particular mutation are shown if that mutation comprises more than 5% of clones in any of the evolutionary rounds.

FIG. 4. Absorption and emission of purified TSFPs. (A) shows purification and expression levels of the different purified proteins. The amounts given correspond to the total amount of purified protein from 60 ml fermentation volume. (B) shows absorption and emission of the purified CGP, various eCGP proteins, and mAG normalized to 1 for the respective peaks. Peak values are provided in TABLE I.

FIG. 5. Thermal stability of evolved fluorescent proteins. (A) Fluorescence profile of the different proteins gradually heated to 99° C. and then allowed to recover at 30° C. Fluorescence was measured every six seconds, and normalized to the fluorescence level at 30° C. (B) Enlargement of fluorescence profile from 90-99° C., showing the persistence of low levels of fluorescence with eCGP123 and eCGP23 at 99° C. (C) Stability with repeated heating and cooling cycles. Proteins were heated to 99° C. for one minute and then cooled to 30° C. for two minutes. This was carried out sixty times and fluorescence was measured at the end of each heating or cooling period. (D) The survival of fluorescent proteins at 80° C. was assessed by heating to 80° C., measuring fluorescence every six seconds. Fluorescence was normalized to the fluorescence level after five minutes at 80° C., at which time the initial rapid loss of fluorescence due to heating stabilized. (E) The survival of fluorescent proteins at 80° C. was assessed by heating to 80° C., and measuring fluorescence each six seconds. Fluorescence was normalized to the fluorescence level after five minutes at 80° C. (FIG. 5D). (F): As FIG. 5E, except proteins were heated to 85° C.

FIG. 6. Stability to chemical denaturation. (A): Each of the fluorescent proteins was diluted into 48 different, Guanidium hydrochloride concentrations, with 7.4 M being the highest concentration. The residual fluorescence was measured at equilibrium, normalized and plotted. The recovered fluorescence was normalized by dividing the fluorescence of corresponding non-denatured samples diluted in parallel. (B): Dependence of the standard free energy of denaturation on guanidine concentration assuming a two-state folding model for the fluorescent proteins (TABLE III). (C): Refolding kinetics. Long-term (2000 s) progress curves for recovery of fluorescence during refolding of Gdn HCl-denatured eCGP123 (blue), CGP (magenta), and mAG (green) upon 20-fold dilution of denatured samples in fresh buffer containing 1 mM DTT at 25° C. (see Methods), with the inset showing the short-term progress curves. Initial rates $V_t$ were obtained from slope at t=0 s of $2^{nd}$-order polynomials fitted to the first 12 s of short-term progress curves. Fluorescence normalized by dividing by final fluorescence value at 15 h.

DETAILED DESCRIPTION OF THE INVENTION

Figure 3:
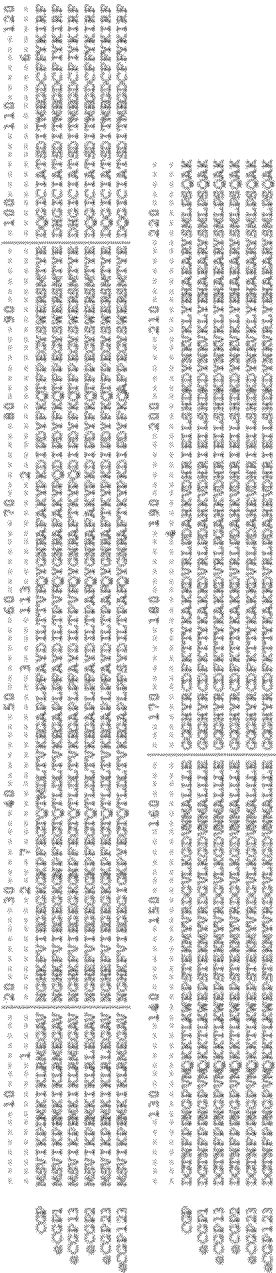
FIG. 3. Sequence alignments of various. TSFPs of the invention, compared to the reference protein, CGP, and to the protein from which CGP was initially derived, mAG (BAD52002). Shown are sequences of CGP [SEQ ID NO: 27], eCGP1 [SEQ ID NO: 6], eCGP13 [SEQ ID NO: 8], eCGP2 [SEQ ID NO: 7], eCGP23 [SEQ ID NO: 9], eCGP123 [SEQ ID NO: 10].

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds. John Wiley & Sons. Inc. 2001. As appropriate, procedures involving the use of commercially available kits and reagents are generally carried out in accordance with manufacturer defined protocols and/or parameters unless otherwise noted.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides or ribonucleotides and polymers thereof ("polynucleotides") in either single- or double-stranded form. Unless specifically limited, the term "polynucleotide" encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts at al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide.

"Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "vector" refers to a nucleic acid molecule capable of transporting another nucleic acid to which it has been linked. For example, one type of vector is a plasmid, a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into, the genome of a host cell upon introduction into the host cell, and thereby are replicated along with the host genome. Certain vectors are capable of directing the expression of genes to which they are operatively linked. Such vectors are referred to herein as "recombinant expression vectors" or "expression vectors".

The term "host cell" (or "recombinant host cell"), as used herein, refers to a cell that has been genetically altered, or is capable of being genetically altered by introduction of an exogenous polynucleotide, such as a recombinant plasmid or vector, and includes not only the particular subject cell but also the progeny thereof. Because certain modifications may occur in succeeding generations due to either mutation or environmental influences, such progeny may not, in fact, be identical to the parent cell, but are still included within the scope of the term "host cell" as used herein.

The term "link" as used herein refers to a physical linkage as well as linkage that occurs by virtue of co-existence within a biological particle, e.g., phage, bacteria, yeast or other eukaryotic cell.

"Physical linkage" refers to any method known in the art for functionally connecting two molecules (which are termed "physically linked"), including without limitation, recombinant fusion with or without intervening domains, intermediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, "linker" or "spacer" refers to a molecule or group of molecules that connects two molecules, such as VH and VL genes or polypeptides (i.e., in a scFv), and serves to place the two molecules in a preferred configuration.

The term "isolated" refers to material which is substantially or essentially free from components which normally accompany the material as it is found in its native or natural state. However, the term "isolated" is not intended refer to the components present in an electrophoretic gel or other separation medium. An isolated component is free from such separation media and in a form ready for use in another application or already in use in the new application/milieu. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "label" and "detectable label" refer to a detectable compound or composition which is conjugated directly or indirectly to the antibody so as to generate a "labeled" or "detectably labeled" antibody. The label may be detectable by itself (e.g. radioisotope labels or fluorescent labels) or, in the case of an enzymatic label, may catalyze chemical alteration of a substrate compound or composition which is detectable. A great number of such labels are known in the art, including without limitation protein tags, radioisotopes, metal chelators, enzymes, fluorescent compounds (dyes, proteins, chemicals), bioluminescent compounds, and chemiluminescent compounds.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Nat'l. Acad. Sci. USA. 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "as determined by maximal correspondence" in the context of referring to a reference SEQ ID NO means that a sequence is maximally aligned with the reference SEQ ID NO over the length of the reference sequence using an algorithm such as BLAST set to the default parameters. Such a determination is easily made by one of skill in the art.

The invention provides novel and highly stable fluorescent proteins. Because the proteins of the invention are particularly stable at very high temperatures, they have been termed Thermostable Fluorescent Proteins, or "TSFPs". Several green TSFPs are disclosed herein, as well as a unique methodology for generating such variants of other proteins, including fluorescent proteins. In particular embodiments disclosed herein, a class of TSFPs termed eCGPs are provided. The eCGPs of the invention were derived from an artificial fluorescent protein previously generated using a consensus engineering approach (consensus green fluorescent protein, or CGP[44]). The invention also provides polynucleotides encoding eCGPs, as well as vectors comprising such polynucleotides and cells transformed or containing such vectors. Various assay methods which utilize the TSFPs of the invention are also encompassed by the invention.

The TSFPs of the invention may be employed for all applications, methods and uses to which GFP and other fluorescent proteins are or may be applied, including their use as markers, as protein tags, in solubility screening, in the generation of split-CGP systems and assays, in protein trafficking and localization assays, in applications involving FRET, and the like. For example, TSFPs may be coupled to antibodies, polynucleotides or other receptors for use in detection assays such as immunoassays or hybridization assays, or to track the movement of proteins in cells. TSFPs may also be useful in systems to detect induction of transcription. For example, a nucleotide sequence encoding a TSFP can be fused to a promoter or other expression control sequence of interest, which can be contained in an expression vector, the construct can be transfected into a cell, and induction of the promoter (or other regulatory element) can be measured by detecting the presence or amount of fluorescence, thereby allowing a means to observe the responsiveness of a signaling pathway from receptor to promoter.

Because the TSFPs of the invention demonstrate remarkable stability in a number of challenging environments, they may find use in processes, assays and other applications in which a high degree of stability is required in order for the fluorescent phenotype to survive. For example, eCGPs show a remarkable degree of thermotolerance. Some of the eCGPs, such as eCGP23 and eCGP123, are able to retain fluorescence after being exposed to very high temperatures. For example, both eCGP23 and eCGP123 are able to recover almost completely after heating at 99° C., a temperature that irreversibly destroys folding in all other fluorescent proteins tested. Similarly, both of these eCGPs are able to retain some degree of fluorescence even at the high temperature of 99° C. Additionally, both of these eCGPs retain approximately 85% of their ambient temperature fluorescence levels for at least 14 hours at 80° C. Thus, these two eCGPs demonstrate remarkable and hitherto unreported levels of thermotolerance for fluorescent proteins, and should find use in various applications for which thermostability as well as increased stability generally are required. Detailed characterization of eCGPs is provided in the Examples which follow.

The fluorescence loss that occurs when fluorescent proteins are heated is caused by a combination of disruption of the local fluorophore environment caused by thermal vibrations and unfolding. Unfolding, in turn, can be either reversible or irreversible. In general, the loss of fluorescence caused by thermal vibrations is almost instantaneously reversible, that caused by reversible unfolding depends upon the kinetics of refolding, while irreversible unfolding does not recover. A number of lines of evidence indicate that most of the loss of fluorescence with heating eCGP123 to 99° C. is due to disruption of the local fluorophore environment, rather than unfolding of the protein. First, a thermal melt does not show the inflection point characteristic of the onset of cooperative unfolding, shown by the other proteins (FIGS. 5a and 5b); secondly, at 99° C., some residual fluorescence is clearly present for eCGP123 and eCGP23, while it is completely lost for the other proteins (FIGS. 5b and 5c); thirdly, upon cooling after the thermal melt, over 60% of the fluorescence returns immediately (FIG. 5a and TABLE II); and finally, when the protein is repeatedly cycled between 99 and 30° C. fluorescence recovery is essentially immediate, and complete, with each cycle (FIG. 5c), while refolding would be expected to take longer. However, although it appears that most of the protein remains folded after short periods at 99° C., it is clear that prolonged incubations at high temperatures below 99° C. can cause significant loss of fluorescence. After 14 hours at 80° C., only 15% of the fluorescence normalized after stabilization at 80° C. is lost (FIG. 5e), whereas at 85° C., only 15% of the fluorescence remains (FIG. 5f).

When the thermal stability of the different evolved eCGP proteins is compared, the increased stability with increased evolution is striking, with the order of stability being eCGP123>eCGP23>eCGP13>eCGP2>eCGP1>CGP: evolution around each additional loop, results in, increased stability. However, the individual loops are not equal in their stabilizing effects, with evolution around loop 2, appearing to provide the greatest individual stabilizing effect (compare eCGP1 to eCGP2 and eCGP13 to eCGP23). In fact, eCGP23 and eCGP123 are extremely similar to one another in their stability.

The eCGPs were also characterized by chemical denaturation using different concentrations of guanidine hydrochloride (FIG. 6a). See also, Example 1, infra.

The invention further provides a method for generating stability-enhanced proteins. The method by which the eCGPs of the invention were generated is explained in detail in the Examples which follow. This method may be applied to other fluorescent proteins, and indeed, to virtually any protein, in order to generate increased-stability variants. Briefly, in the method of the invention, a recursive directed evolution strategy is employed, in which single destabilizing inserts are grafted into exposed loops of the protein in such a way that upon each insertion, folding and function are significantly affected but not destroyed (FIG. 1A). Upon overcoming the effect of a single insert by the initial round of evolution, the procedure is repeated with additional destabilizing inserts in an iterative fashion. The method enables one to overcome a final destabilizing force that would completely destroy both folding and function if applied in a single step.

The application of this method to a fluorescent protein is facilitated by the ease with which screening for correct folding can be carried out. However, this method is likely to be generally applicable to any protein, providing three criteria are fulfilled: 1) Surface exposed insert sites are correctly identified; 2) An appropriate destabilizing insert is used; and 3) A method to select correctly folded clones is available. In the example used herein, the structure of mAG, which was used to derive CGP, allowed the modeling and identification of the surface exposed loops. Although this is the ideal situation, when a structure or model are not available, it is possible that the application of secondary[75, 76] or tertiary structural prediction methods[77, 78] may provide sufficient information to identify suitable surface turns, since it is extremely unlikely that inserts placed within the protein core could be overcome by any degree of evolution.

The destabilizing insert used to generate the exemplified TSFPs disclosed herein here was based on an antibody heavy chain complementarity determining region 3 (HCDR3). This insert was chosen as the N and C termini of HCDR3s are close to one another within the context of an anti-parallel beta strand[67], thereby presumptively providing destabilization without completely inhibiting folding. It is likely that alternative inserts could also provide appropriate degrees of destabilization, and it is possible that a panel of destabilizing inserts could be developed. In fact, such inserts could even comprise whole proteins in which the N and C termini were close to one another.

In the practice of the method of the invention, it is important to identify or develop a method to select or screen for correctly folded clones. When applied to fluorescent proteins, it is relatively straightforward to examine bacterial clones for fluorescence. A similar approach could be used for enzymes which can be expressed in bacteria, and for which calorimetric or fluorescent reagents are available. However, for the majority of proteins for which there is no obvious directly screenable phenotype, a separate screen for correct folding is required. This is not unlike the use of phage[79-81] or yeast display[82-85] to identify amino acids comprising specific binding sites: it is not sufficient to identify clones no longer binding to the binding partner, since loss of binding may be due to lack of folding. In addition to the negative selection for loss of binding, a positive selection for correct folding must also be included in the selection strategy. In the case of yeast, it is relatively straightforward, as only correctly folded proteins reach the cell surface and poorly folding proteins are retained in the endoplasmic reticulum. As a result it is sufficient to detect surface display using monoclonal[83], polyclonal[82] or anti-tag[84] antibodies. In the case of phage display, recognition of conformational epitopes.

The invention also provides various methods which utilize TSFPs and TSFP coding sequences, such methods being currently employed with various other fluorescent proteins and variants thereof. For example, the invention provides a method for identifying the presence of a molecule in a sample. Such a method can be performed, for example, by linking a fluorescent protein variant of the invention to the molecule, and detecting fluorescence due to the fluorescent protein variant in a sample suspected of containing the molecule. The molecule to be detected can be a polypeptide, a polynucleotide, or any other molecule, including, for example, an antibody, an enzyme, or a receptor, and the like. The sample to be examined can be any sample, including a biological sample, an environmental sample, or any other sample for which it is desired to determine whether a particular molecule is present therein.

TSFPs may be linked to the molecule directly or indirectly, using any linkage that is stable under the conditions to which the protein-molecule complex is to be exposed. Thus, a TSFP and the subject molecule can be linked via a chemical reaction between reactive groups present on the protein and molecule, or the linkage can be mediated by linker moiety, which contains reactive groups specific for the fluorescent protein and the molecule. It will be appreciated that the appropriate conditions for linking a TSFP and the molecule are selected depending, for example, on the chemical nature of the molecule and the type of linkage desired. Where the molecule of interest is a polypeptide, a convenient means for linking a TSFP and the molecule is by expressing them as a fusion protein from a recombinant nucleic acid molecule, which comprises a polynucleotide encoding, for example, an eCGP operatively linked to a polynucleotide encoding the polypeptide molecule.

TSFPs may also be used in methods to identify, agents and/or conditions that regulate the activity of an expression control sequence. Such methods may be performed, for example, by exposing a recombinant nucleic acid molecule, which includes a polynucleotide encoding a TSFP operatively linked to an expression control sequence, to an agent or condition suspected of being able to regulate expression of a polynucleotide from the expression control sequence, and detecting fluorescence of the TSFP due to such exposure. Such methods may be useful for identifying chemical or biological agents, including cellular proteins, that can regulate expression from the expression control sequence, including cellular factors involved in the tissue specific, expression from the regulatory element. As such, the expression control sequence can be a transcription regulatory element such as a promoter, enhancer, silencer, intron splicing recognition site, polyadenylation site, or the like; or a translation regulatory element such as a ribosome binding site.

The invention also provides conservatively modified variants, as will be understood the those skilled in the art. Conservative substitutions may be tested using assays described herein or otherwise well known in the art. Other eCGP variant proteins can be identified, for example, using methods described in WO0123602 and other methods to select for increased folding. For example, to obtain an eCGP variant with increased folding ability, a "bait" or "guest" peptide that decreases the folding yield of the eCGP is linked to the eCGP. The guest peptide can be any peptide that, when inserted, decreases the folding yield of the eCGP, which may be measured by fluorescence, for example. A library of mutated fluorescent proteins is created. The bait peptide is inserted into the eCGP and the degree of fluorescence of the protein is assayed. Those clones exhibit increased fluorescence relative to a fusion protein comprising the bait peptide and parent eCGP are selected (the fluorescent intensity reflects the amount of properly folded fluorescent protein). The guest peptide may be linked to the eCGP at an end, or may be inserted at an internal site.

Various techniques for introducing mutations are well known in the art. These include, but are not limited to, such techniques as error-prone PCR, chemical mutagenesis, and cassette mutagenesis. Alternatively, mutator strains of host cells may be employed to add mutational frequency (Greener and Callahan, 1995, Strategies in Mol. Biol. 7: 32). For example, error-prone PCR (see, e.g., Ausubel, supra) uses low-fidelity polymerization conditions to introduce a low level of point mutations randomly over a long sequence. Other mutagenesis methods include, without limitation, recombination, oligonucleotide-directed mutagenesis, phosphothioate-modified DNA mutagenesis, mutagenesis using uracil-containing templates, mutagenesis using gapped duplex DNA, point mismatch repair, mutagenesis using repair-deficient host strains, and deletion mutagenesis. Kits for mutagenesis are commercially available (e.g., Bio-Rad, Amersham International). More recent approaches include codon-based mutagenesis, in which entire codons are replaced, thereby increasing the diversity of mutants generated, as exemplified by the RID method described in Murakami et al., 2002, Nature Biotechnology, 20: 76-81.

The TSFP polypeptides may be prepared using methods well known in the art, including by peptide synthesis and recombinant production means. For example, an eCGP may be synthesized according to standard solid-phase methodologies, utilizing the amino acid sequences provided herein, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

Also provided are vectors containing the TSFP polynucleotides of the invention, as well as host cells transformed or transfected with, or otherwise made to contain, such vectors. Also provided is a recombinant nucleic acid molecule, which includes at least one polynucleotide encoding a TSFP operatively linked to one or more other polynucleotides. The one or more other polynucleotides can be, for example, a transcription regulatory element such as a promoter or polyadenylation signal sequence, or a translation regulatory element such as a ribosome binding site. Such a recombinant nucleic acid molecule can be contained in a vector, which can be an expression vector, and the nucleic acid molecule or the vector can be contained in a host cell. A vector of the invention will generally contain various elements required for replication in a prokaryotic or eukaryotic host system, or both, as required. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a number of commercial sources or constructed using methods well known in the art.

The disclosed eCGPs, eCGP variants, or fusions of an eCGP and another polypeptide, may conveniently expressed in a suitable host cell, such as an *E. coli* cell, using an eCGP-encoding polynucleotide, such as the DNA coding sequences for eCGPs provided in the TABLE OF SEQUENCES, infra.

There are many expression systems for producing the proteins of the invention that are well know to those of ordinary skill in the art. (See, e.g., *Gene Expression Systems*, Fernandes and Hoeffler, Eds. Academic Press, 1999; Russell & Sambrook, supra). Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems, the tryptophan (trp) promoter, the tac promoter and the lambda-derived $P_L$ promoter and N-gene ribosome binding site. The particular promoter system is not critical to the invention, any available promoter that functions in prokaryotes can be used. Standard bacterial expression vectors include plasmids such as pET, pTET, pBR322-based plasmids, e.g., pBLUESCRIPT™, pSKF, pET23D, λ-phage derived vectors, p15A-based vectors and fusion expression systems such as GST. Epitope tags can also be added to recombinant proteins to provide convenient methods of isolation, e.g., c-myc, HA-tag, 6-His tag, maltose binding protein, VSV-G tag, anti-DYKDDDDK tag, or any such tag, a large number of which are well known to those of skill in the art.

For expression of fusion polypeptides in prokaryotic cells other than *E. coli*, regulatory sequences for transcription and translation that function in the particular prokaryotic species is required. Such promoters can be obtained from genes that have been cloned from the species, or heterologous promoters can be used. For example, the hybrid trp-lac promoter functions in *Bacillus* in addition to *E. coli*. These and other suitable bacterial promoters are well known in the art and are described, e.g., in Russell & Sambrook and Ausubel et al. Bacterial expression systems for expressing the proteins of the invention are well known and commercially available.

Similarly, the for expression of fusion polypeptides in eukaryotic cells, transcription and translation sequences that function in the particular eukaryotic species are required. For example, eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include those employing the CMV promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the polypeptide is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

Inducible promoters for other organisms are also well known to those of skill in the art. These include, for example, the metallothionein promoter, the heat shock promoter, as well as many others.

Translational coupling may be used to enhance expression as is well known. The strategy uses a short upstream open reading frame derived from a highly expressed gene native to the translational system, which is placed downstream of the promoter, and a ribosome binding site followed, after a few amino acid codons by a termination codon. Just prior to the termination codon is a second ribosome binding site, and following the termination codon is a start codon for the initiation of translation. The system dissolves secondary structure in the RNA, allowing for the efficient initiation of translation.

The construction of polynucleotide constructs generally requires the use of vectors able to replicate in host bacterial cells, or able to integrate into the genome of host bacterial cells. Such vectors are commonly used in the art. A great number of systems and kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The TSFP polypeptides can be expressed intracellularly, or can be secreted from the cell. Intracellular expression often results in high yields. If necessary, the amount of soluble, active fusion polypeptide may be increased by performing refolding procedures (see, e.g. Sambrook et al., supra.: Marston at al., *Bio/Technology* (1984) 2:800; Schoner at al., *Bio/Technology* (1985) 3: 151). Fusion polypeptides of the invention can be expressed in a variety of host cells, including *E. coli*, other bacterial hosts, yeast; and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the recombinant polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)).

To facilitate purification of the TSFP polypeptides of the invention, the nucleic acids that encode the fusion polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells).

Additional expression vectors suitable for attaching a tag to the fusion proteins of the invention, and corresponding detection systems are known to those of skill in the art, and several are commercially available (e.g., FLAG" (Kodak, Rochester N.Y.). Mother example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli. E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Various aspects of the invention are further described and illustrated by way of the several examples which follow, none of which are intended to limit the scope of the invention.

EXAMPLES

Example 1

Generation and Characterization of Evolved Consensus Green Fluorescent Proteins

Materials and Methods:
CDR3 Insertions into CGP

The 60-bp CDR3 sequences were inserted into CGP [SEQ ID NO: 27] by PCR assembly. The PCR primers generally contained a 20-bp long CGP specific sequence and a 40-bp 5' tail encoding one part of the CDR3. The two CDR3 containing primers had a 20-bp homologous overlapping sequence to facilitate PCR assembly. The following general procedure was used, unless otherwise described. The reaction was performed in 50 µl containing 1× Thermopol buffer (NEB), 250 µM dNTP, 0.5 µM of each primers and 1.25 U Taq polymerase (NEB) with cycling conditions as follows: 1 min initial denature at 94° C., then 30 cycles of 94° C., 15 sec, 55° C., 15 sec, 30 sec, 72° C., then a final elongation of 5 min at 72° C. TABLE IV contains the primer sequences. The nucleotide sequence encoding the 20 amino acid long CDR3 sequence was different for each insert, using different codons, in order to prevent homologous recombination in the bacteria. Inserting single CDR3s into CGP [SEQ ID NO: 27] was achieved by performing two PCR reactions with 1) CGP-5' and CDR-loop-x-R-CGP and 2) CDR-loop-x-F-CGP and CGP-3' primers. The x denotes the loop number. The resulting bands were gel purified and assembled in an assembly reaction with CGP-5' and CGP-3' primers added after 25 cycles.

Multiple CDR3s were inserted similarly. The double inserted libraries were assembled from 3 fragments; the triple inserted libraries used 4 fragments. For example the double library containing CDR3 insert in loop 1 and loop 3 were assembled from fragments amplified using these primers; 1) CGP-5' and CDR-loop-1-R-CGP; 2) CDR-loop1-F-CGP and CDR-loop-3-R-CGP; 3) CDR-loop-3-F-CGP and CGP-3' (see TABLE IV). Other libraries were created similarly using the appropriate primers.

DNA Shuffling

DNA shuffling was performed according to Zhao, 1997[91]. Briefly, 10 µg of template DNA, CGP [SEQ ID NO: 27] containing 1, 2 or 3 CDR3 inserts, were digested with 1 U of DnaseI (NEB) for 10 minutes at 15° C. in 50 mM Tris-Ac pH 7.5, 2 mM $CoCl_2$. The reaction was terminated by heating for 3 minutes at 90° C., and DNA fragments purified by spin-column chromatography on Sephadex-25 (GE Healthcare) columns. The digested template was assembled in a primer-less PCR reaction with 1.25 U Pfu Exo⁻ DNA polymerase (Stratagene) using 15 µl of the digested template in a buffer containing 1×Pfu reaction buffer, 0.4 mM dNTP in a 25 µl reaction volume. The cycling conditions were 97° C., 3 min initial denature, then 35 cycles of 96° C. 25 sec, 56° C. 25 sec, 72° C. 1 min, with a final extension for 5 min at 72° C. 3 µl of the amplification reaction was amplified by 2.5 U Taq polymerase (NEB) in a 100 µl reaction containing 1× Thermopol buffer (NEB), 250 µM dNTP, 0.5 µM of CGP-5' and CGP-3' primers with the following cycling: 1 minute initial denature at 94° C., then 30 cycles of 94° C., 15 see; 60° C., 15 sec; 72° C. 30 sec; with a final elongation for 5 minutes at 72° C. The PCR product was phenol/chloroform extracted and purified by spin-columns containing Sephadex G-75 (GE Healthcare). The purified DNA was digested with BssHII (NEB) and NheI (NEB) according to the manufacturers recommendation and cloned into pETCK3 (Kiss et al., 2006[88]). The ligation was electroporated into BL21(DE3) Gold electrocompetent cells. The cells were plated on nitrocellulose filters on LB agar plates containing 50 µg/ml kanamycin and 3% glucose and grown overnight at 37° C. The filters were transferred onto kanamycin LB plates containing 1 µg/ml IPTG and induced for 4 hours at 30° C. Colonies that were greenest after induction were picked and sequenced. The selected clones for the next round of shuffling were pooled and the CDR3 sequences were recreated by PCR assembly using CDR3 specific primers that lacked any CGP [SEQ ID NO: 27] specific sequences.

Protein Expression and Purification

Plasmids encoding the fluorescent proteins cloned into pETCK3 were transformed into *E. coli* BL21 DE3 cells (Stratagene). Single colony transformants were cultured overnight at 37° in Luria Broth with 50 µg/ml kanamycin. The overnight cultures were suspended in fresh Terrific Broth containing 50 µg/ml Kanamycin and transferred to the Kalypsis Airlift Fermentation. System, based on the system described by Lesley et al[89]. Cultures were grown at 37° for 3 hours (optical density of 1.5-2.5 (600 nm)) on 100% air. The temperature was reduced to 30° and IPTG added to a final concentration of 1 mM. After 4 hour of growth, 50% air and 50% oxygen, cells were harvested by centrifugation and the resulting pellets were stored overnight at −20°. The bacteria pellets were removed from storage, thawed, and suspended in lysis buffer (500 mM NaCl, 5 mM Imidazole). Cells were lysed by sonication in the Kalypsis pre-chilled rotor, using 4 cycles of one minute sonication (duty cycle 100, amplitude 75) followed by one minute rest, then centrifuged at 7000×g for 30 min. The Kalypsis Robot transferred the supernatant to the nickel columns (Nickel. Chloride bound to GE Chelating Sepharose Fast Flow Resin) which were washed with (500 mM NaCl, 5 mM Imidazole). The bound proteins were eluted with (500 mM NaCl, 500 mM Imidazole).

The fluorescence of the purified proteins was measured (SPECTRAFluor Plus, 492 nm, optimal gain 44) in arbitrary fluorescence units measured at 535 nm. An SDS-PAGE gel was loaded with samples based on equal fluorescence and proteins were quantified against protein standards, using the Syngene GeneTool Software.

Thermostability Measurements

Proteins of equal fluorescence were diluted into 50 µl of TNG buffer (100 mM Tris-Ac pH 7.5, 100 mM NaCl, 10% glycerol) and placed into 0.2 ml thin wall PCR tubes. Thermal cyclings were performed in a Rotor-Gene 6000 real time PCR machine (Corbett Life Science). Fluorescence and gain were adjusted so that the fluorescence of the starting samples was between 90-100. The melting profile was resolved between 30° C. and 99° C. Temperature was raised by 0.5° C. increments. The samples were incubated at each temperature for 60 sec.

Single Molecule Spectroscopy

Fluorescence Correlation Spectroscopy was performed in the same setup described previously[44]. Quantum yield was determined relative to Fluorescein from the ratio of integrated fluorescence signal to the absorbance at 488 nm.

Chemical Denaturation

Equilibrium fluorescence values were measured by diluting guanidine hydrochloride denatured eCGP variants into TNG containing 5 mM DTT to various final guanidine concentrations between 1 and 8 M in increments of 0.15 M guanidine, and allowing refolding to proceed at 15° C. Fluorescence values were measured using a FL600 Microplate Fluorescence Reader (488-nm excitation, 530-nm emission, 10-nm band pass) and scaled by dividing by the fluorescence levels of corresponding nondenatured samples diluted in parallel as a reference. Midpoint recovery concentrations of guanidine Cm (recovery of 50% of the initial fluorescence) were determined from sigmoidal fits using SOLVER in EXCEL, to the scaled fluorescence value F using the equation $F_j = a+b/(1+(C_j/C_m)h)$, where a, b, Cm and h are adjustable parameters, and Cj is the molarity of the guanidine in the refolding experiment j. The data were used to calculate the dependence of the standard free energy of denaturation, $DG1 = -RT \ln K$, on guanidine concentration, where R is the gas constant, T is the absolute temperature and K is the equilibrium constant, which can be calculated from the experimental data by using the standard equation $K = [(y)N-(y)]/[(y)-(y)D]$, where (y) is the observed value of the parameter used to follow unfolding, and (y)N and (y)D are the (y) values for the native state and the denatured state, respectively, under the same conditions under which (y) was measured.

Results

Evolutionary Strategy

A recursive evolutionary strategy was employed, in which single inserts were grafted into exposed loops in such a way that upon each insertion, folding and function were significantly affected but not destroyed (FIG. 1A). This provides a baseline which may be improved by evolution. Upon overcoming the effect of a single insert, the procedure is then repeated with a second, and finally a third insert. In this way it is possible to overcome a final destabilizing force that would completely destroy both folding and function if applied in a single step.

This method was applied to CGP [SEQ ID NO:27] by modeling the structure of this protein on that of Dronpa, the closest fluorescent protein for which a structure has been determined (Wilmann et al., 2006[90]), and targeting three identified beta turns for insertion. These were termed loop 1 (V18/N19), loop 2 (E96/D97) and loop 3 (E164/G165). The destabilizing insert used was based on a human heavy chain third antibody complementarity determining region (HCDR3) sequence. Although HCDR3s are highly diverse loops, they are embedded into a relatively conserved beta sheet structure[66], as a result of which the amino acids at either end (cysteine 104 and tryptophan 119; IMGT numbering[67] are always joined by two hydrogen bonds. As the usual distance between these two amino acids is similar to that between amino acids just before the turns described above, it was presumed that the insertion of such a sequence into a CGP loop would probably be disruptive to folding, but would not destroy it completely. In order to avoid the presence of an unpaired cysteine (the HCDR3 N terminal cysteine normally disulfide bonds with another cysteine in framework one), this codon was mutated to a serine, which is able to form the same hydrogen bonds. The final sequence used (SARSFYLQSD-LAAGDFDSWG) [SEQ ID NO: 26] based on a randomly picked HCDR3 with a few internal changes to facilitate cloning, was inserted at V18/N19 and E96/D97 in two independent PCR assemblies. As expected, this resulted in a significant reduction in the fluorescence of induced bacterial colonies as shown in FIG. 1B.

After three rounds of error prone PCR, and DNA shuffling on these two modified genes, the fluorescence of induced bacterial colonies increased significantly, some reaching the levels of the original CGP protein (FIG. 1B). During the mutation and selection process, the gene was always reassembled using the HCDR3 as an anchor, in order to force mutations into the CGP and not the inserted HCDR3. After three rounds, PCR assembly was again used to insert the same HCDR3 amino acid sequence at position E164/G165 of the genes from 23 fluorescent evolved clones containing an insert at V18/N19 and 22 clones containing an insert at E96/D97. The DNA sequence encoding the HCDR3 insert was altered to avoid recombination with the first insert. A significant reduction in fluorescence was again observed, which could be restored after three further rounds of evolution, carried out as before by PCR assembly of now three fragments using the two HCDR3 inserts as anchors.

The process was repeated a final time, pooling fluorescent colonies and inserting the HCDR3 into three sites (V18/N19, E96/D97 and E164/G165). With the proteins containing three inserts, four rounds of evolution were required before fluorescence was significantly restored. After each round of evolution approximately 100 clones were sequenced, allowing analysis of the accumulated mutations (FIG. 2). It should be pointed out that although the use of assembly PCR to insert each additional loop into CGP [SEQ ID NO: 27] allowed mutations accumulated in previous rounds to persist into the following evolutionary rounds, this was not true of those mutations close to the insert site, which were "overridden" by the primers used for insertion in the first round. In subsequent rounds, the HCDR3 insertion sequences themselves were used for assembly, allowing reappearance of mutations close to insertions. In general 4 classes of mutations were observed: 1) those (e.g. D7E, M40L, T59P, V60A) appearing immediately and retained throughout; 2) those which first appear with a single insert, are specific for that insert (e.g. 098H for 18/19 inserts, and K22E for 96/97 inserts), are retained in the presence of two inserts, but are then lost when three inserts are present; 3) those appearing in the presence of two inserts, and persisting in the presence of three inserts (e.g. E164K, K190E, K208R); and 4) those (e.g. A175, K30I, F34Y, A53S) which are only found when three inserts are present.

Gene Synthesis

Genes corresponding to the proteins without inserts were synthesized (Blue Heron Biotechnology) for each of the five evolutionary paths (FIG. 1A). Synthesized genes contained those mutations that led to amino acid changes in at least 20% of sequences, and silent mutations found in greater than 90% of sequences. In addition, one silent mutation frequently found adjacent to a non-silent mutation was also included. In order to concentrate on mutations responsible for global increases in stability, rather than mutations responding to specific changes in secondary structure adjacent to the insert site, those mutations found within two amino acids of an insertion point were not included, even though there are examples of mutations in loops (e.g. Y39N in sfGFP[7]) which are globally stabilizing.

The aligned amino acid sequences of the final genes synthesized, compared to CGP [SEQ ID NO: 27], are shown in FIG. 3. As can be seen, some mutations (eight of eighteen) recapitulate amino acids found in fluorescent proteins used to create the CGP consensus sequence. The remaining ten mutations are equally split between those found in mAG (and modified for CGP) and those not previously found in any other fluorescent protein, and unique to these evolved proteins. Of the mutations which revert back to mAG, three (D7E, M40L, A69T) are found in most of the evolved proteins, while the remaining two (K32N and F34Y) are each found in only one or two of the proteins. The reversion of such presumably destabilizing mutations in consensus sequences is similar to those found in other examples[37-40], and underlie the importance of examining the roles of individual amino acids for their contributions to stability.

Properties of eCGPs

The five fluorescent protein genes were cloned into pETCK3[88] and expressed in BL21. All were able to direct the synthesis of fluorescent proteins at levels comparable to, or exceeding, CGP and mAG (FIG. 4a). The excitation/emission properties (FIG. 4b and TABLE I) of the proteins were similar to either CGP [SEQ ID NO: 27] (eCGP1 [SEQ ID NO: 6] and eCGP2 [SEQ ID NO: 7]) or mAG (eCGP13 [SEQ ID NO: 8], eCGP23 [SEQ ID NO: 9] and eCGP123 [SEQ ID NO: 10), with the CGP series being slightly red shifted compared to the mAG series. The quantum yields of the proteins ranged from 0.54 (eCGP1) [SEQ ID NO: 6] to 0.75 (eCGP13) [SEQ ID NO: 8], not too dissimilar to that of mAG (0.83). All proteins were monomeric as determined by gel filtration (not shown) or fluorescence correlation spectroscopy (TABLE I).

In a first test of protein thermostability, the proteins were slowly melted at 0.5° C./min, using a real time PCR machine (Rotor-Gene 6000, Corbett Life Sciences, FIG. 5a) which monitored fluorescence changes with temperature in real time. The temperature was gradually increased to 99° C., and then returned to 30° C., to monitor recovery. After approximately 38° C., all proteins showed a reduction in fluorescent with increasing temperature as shown in FIG. 5a. This fluorescence loss is characteristic of fluorescent proteins, and thought to be due to two components: changes in the immediate fluorophore environment caused by increased thermal vibrations, and unfolding of the proteins. Fluorescence loss due to the former are immediately reversible and do not represent unfolding[68,69], while fluorescence loss due to the latter require refolding for fluorescence to return. As temperature increases, the proportion of fluorescence loss due to these two components will vary, depending upon the stability of the protein and the temperature. In general, little of the fluorescence loss is caused by unfolding until the temperature at which cooperative unfolding starts is reached. This is recognized as an inflection point in the melting curve, and represents the point at which unfolding suddenly accelerates. This is similar to changes in CD spectra observed with increasing temperature[70].

All proteins, with the exception of eCGP23 [SEQ ID NO: 9] and eCGP123 [SEQ ID NO: 10], showed cooperative unfolding as the temperature was increased, with inflection points between 73 and 87° C., cooperative transition midpoints two to three degrees later, and characteristic steeper denaturation curves[69]. eCGP23 [SEQ ID NO: 9] and eCGP123 [SEQ ID NO: 10] were characterized by the absence of a clear cooperative transition, and even at 99° C., some fluorescence remained (FIG. 5b). Recovery upon cooling to 30° C. resulted in essentially complete (96%) recovery of eCGP123 [SEQ ID NO: 10], and 85% recovery of eCGP23 [SEQ ID NO: 9] (TABLE II). The remaining proteins recovered to varying degrees, depending upon the degree of evolution. For all the evolved proteins, 54-61% of the fluorescence recovery occurred instantaneously, while for mAG and CGP, the instant recovery was lower (35% and 44% respectively).

The same order of stability was observed when the proteins were treated with multiple heat cool cycles (equivalent to 60 "PCR cycles" with 1 minute denaturation at 99° C. and 2 minutes recovery at 30° C.—FIG. 5c for CGP [SEQ ID NO: 27] and eCGP123 [SEQ ID NO: 10]). eCGP123 [SEQ ID NO: 10] and eCGP23 [SEQ ID NO: 9] continued to show low levels of fluorescence at 99° C., while the other proteins rapidly lost fluorescence at this temperature. After 60 heat/cool cycles, and at each return to 30° C., the fluorescence of the two stable proteins returned to their pretreatment levels, while the remaining proteins showed a dramatic drop after the first heat cycle, with fluorescence further decreasing to zero with additional cycles, and little recovery upon return to 30° C.

One last test of thermal stability was the ability of the proteins to resist high temperature for prolonged periods. The proteins were all heated to 80° C. or 85° C. This resulted in the initial rapid loss of over 80% fluorescence due to thermal vibration, which stabilized after about six to seven minutes. The fluorescence of the different proteins was normalized at this time (arrow FIG. 5d), and further fluorescence loss monitored for 14 hours. eCGP123 [SEQ ID NO: 10] and eCGP23 [SEQ ID NO: 9] lost approximately 15% fluorescence after 14 hours at 80° C., while all the other proteins, with the exception of eCGP13 [SEQ ID NO: 8] which was intermediate, had lost all fluorescence by 2-3 hours (FIG. 5e). At 85° C. the fluorescence loss of the less stable proteins. (CGP [SEQ ID NO: 27], eCGP1 [SEQ ID NO: 6] and mAG) was complete by five minutes. eCGP1 [SEQ ID NO: 6] and eCGP13 [SEQ ID NO: 8] showed complete loss of fluorescence by three hours, while after 14 hours eCGP23 [SEQ ID NO: 9] and eCGP123 [SEQ ID NO: 10] still retained approximately 10-15% of the normalized fluorescence at 85° C. (FIG. 5F).

Thermal denaturation was monitored using measures independent of intrinsic fluorescence. However, the Thermofluor assay[71, 72] was unsuccessful due to degradation of the Sypro Orange at temperatures above 80° C., and it also proved impossible to carry out circular dichroism at the high temperatures required.

eCGP stability was also studied by denaturation in guanidine hydrochloride (FIG. 6A and TABLE III) with unfolding monitored by fluorescence. At equilibrium, which required over two weeks, eCGP123 [SEQ ID NO: 10] and eCGP23 [SEQ ID NO: 9] were again the most stable proteins, with melting (kd) occurring at 6.45 M guanidine for eCGP123 [SEQ ID NO: 10] and 6.19 M for eCGP23 [SEQ ID NO: 9]. However, the order of stability for the remaining proteins was slightly different to that observed with thermal denaturation, with eCGP2 [SEQ ID NO: 7] being significantly more stable than eCGP13 [SEQ ID NO: 8], and CGP [SEQ ID NO: 27] being more stable than eCGP1 [SEQ ID NO: 6]. By extrapolating a natural log fit of the sigmoidal denaturation curve to infinite dilution (FIG. 6B), the ΔG was determined, which again showed eCGP123 [SEQ ID NO: 10] to be by far the most stable protein at 12.4 kcal/mol.

CGP [SEQ ID NO: 27], mAG, and eCGP123 [SEQ ID NO: 10], representing the starting, evolved, and closest natural proteins, were also analyzed for folding kinetics. Proteins were denatured in Gdn HCl, and fluorescence recovery monitored upon dilution into fresh buffer. Although CGP [SEQ ID NO: 27] is much less stable than mAG, it displayed an approximately 3.5-fold faster initial rate for fluorescence recovery relative to the more stable mAG (FIG. 6C, inset). This faster folding behavior is consistent with the observation that CGP also unfolds much faster than mAG in 8 M Gdn HCl as noted above. Such behavior is typical of simple two-state folders, for which increased forward folding rate is mirrored by a corresponding increased unfolding rate.

eCGP123 [SEQ ID NO: 10] folds 4-fold faster than CGP [SEQ ID NO: 27]. The increased stability of eCGP123 [SEQ ID NO: 10] relative to CGP [SEQ ID NO: 27] likely results from the very slow unfolding of eCGP123 [SEQ ID NO: 10] consistent with the slow approach to equilibrium during the equilibrium Gdn HCl unfolding experiments and the thermal stability.

TABLES

TABLE I

|  | Absorption max (nm) | Emission max (nm) | Q.Y. | $R_0$, nm |
|---|---|---|---|---|
| CGP [SEQ ID NO: 27] | 503 | 515 | 0.66 | 20.3 |
| eCGP1 [SEQ ID NO: 6] | 504 | 514 | 0.54 | 19.3 |
| eCGP2 [SEQ ID NO: 7] | 501 | 511 | 0.59 | 22.9 |
| eCGP13 [SEQ ID NO: 8] | 493 | 505 | 0.75 | 20.9 |
| eCGP23 [SEQ ID NO: 9] | 493 | 504 | 0.73 | 16.6 |
| eCGP123 [SEQ ID NO: 10] | 493 | 504 | 0.69 | 21.3 |
| mAG | 491 | 505 | 0.83 | 18.6 |

TABLE II

RECOVERY AFTER THERMAL MELT

|  | % instant recovery | % final recovery | instant recovery as % of total recovery |
|---|---|---|---|
| eCGP123 [SEQ ID NO: 10] | 58.8 | 96.0 | 61.3 |
| eCGP23 [SEQ ID NO: 9] | 47.7 | 85.5 | 55.8 |
| eCGP13 [SEQ ID NO: 8] | 33.4 | 55.2 | 60.5 |
| eCGP2 [SEQ ID NO: 7] | 12.0 | 22.3 | 53.8 |
| eCGP1 [SEQ ID NO: 6] | 15.0 | 27.0 | 55.6 |
| CGP [SEQ ID NO: 27] | 8.0 | 18 | 44.4 |
| mAG | 7.5 | 21.3 | 35.2 |

TABLE III

STABILITY BY GUANIDINE DENATURATION

| | kd [GnHCl] | h | ΔG(H$_2$O) | m |
|---|---|---|---|---|
| CGP [SEQ ID NO: 27] | 2.56 | 9.71 | 4.9 ± 0.1 | 1.9 ± 0.05 |
| eCGP1 [SEQ ID NO: 6] | 2.12 | 12.45 | 6.1 ± 0.0 | 2.9 ± 0.02 |
| eCGP2 [SEQ ID NO: 7] | 5.12 | 15.53 | 8.5 ± 0.5 | 1.7 ± 0.10 |
| eCGP13 [SEQ ID NO: 8] | 3.15 | 11.08 | 5.9 ± 0.1 | 1.9 ± 0.04 |
| eCGP23 [SEQ ID NO: 9] | 6.19 | 14.43 | 9.8 ± 1.4 | 1.6 ± 0.23 |
| eCGP123 [SEQ ID NO: 10] | 6.45 | 14.29 | 12.4 ± 2.2 | 2.0 ± 0.33 |
| mAG | 5.86 | 16.66 | 8.9 ± 0.9 | 1.5 ± 0.15 |

TABLE IV

OLIGONUCLEOTIDES USED

| Name | Oligo Sequence |
|---|---|
| CDR3-loop1-F | CTTGCAATCCGATCTTGCAGCAGGTGACTTCGACTCTTGGGGT [SEQ ID NO: 11] |
| CDR3-loop1-F-CGP | CTTGCAATCCGATCTTGCAGCAGGTGACTTCGACTCTTGGGGTAACGGCCATAAATTTGTAATTG [SEQ ID NO: 12] |
| CDR3-loop1-R | CACCTGCTGCAAGATCGGATTGCAAGTAGAAGCTACGAGCACT [SEQ ID NO: 13] |
| CDR3-loop1-R-CGP | CACCTGCTGCAAGATCGGATTGCAAGTAGAAGCTACGAGCACTAACGGCACCTTCCATACGC [SEQ ID NO: 14] |
| CDR3-loop2-F | CCTCCAAAGTGACTTAGCTGCCGGCGATTTTGATAGCTGGGGC [SEQ ID NO: 15] |
| CDR3-loop2-F-CGP | CCTCCAAAGTGACTTAGCTGCCGGCGATTTTGATAGCTGGGGCGATCAAGGAATTTGTATCGC [SEQ ID NO: 16] |
| CDR3-loop2-R | CGCCGGCAGCTAAGTCACTTTGGAGGTAAAATGAGCGGGCCGA [SEQ ID NO: 17] |
| CDR3-loop2-R-CGP | CGCCGGCAGCTAAGTCACTTTGGAGGTAAAATGAGCGGGCCGATTCATAGGTCATAGAGCGTTC [SEQ ID NO: 18] |
| CDR3-loop3-F | TTTACAGTCTGACTTGGCGGCTGGGGATTTCGATTCGTGGGGG [SEQ ID NO: 19] |
| CDR3-loop3-F-CGP | TTTACAGTCTGACTTGGCGGCTGGGGATTTCGATTCGTGGGGGGAGGTGGACACTACCGCTG [SEQ ID NO: 20] |
| CDR3-loop3-R | CCCCAGCCGCCAAGTCAGACTGTAAATAGAAAGACCGCGCAGA [SEQ ID NO: 21] |
| CDR3-loop3-R-CGP | CCCCAGCCGCCAAGTCAGACTGTAAATAGAAAGACCGCGCAGATTCGAGCAGAAGTGCCATG [SEQ ID NO: 22] |
| CGP-3' | TTTGCCGCTAGCTTTAGCCTGAGACGGTAACATAGAATAGC [SEQ ID NO: 23] |
| CGP-5' | TACATATGGGCGCGCATGCCTCAGTAATTAAACCG [SEQ ID NO: 24] |

TABLE OF DNA AND PROTEIN SEQUENCES eCGP DNA Sequences:

eCGP1 [SEQ ID NO: 1]

```
  1    ATGTCAG TAATTAAACC GGAAAT-
       GAAA ATTAAATTGC GTATGGAAGG TGCCGTTAAC GGCCATAAAT TTGTAATTGA AGGGGAAGGA
       AAAGGCAACC

98    CATTCGAAGG AACCCAGACC CTGGATT-
       TAA CCGTAAAAGA AGGCGCACCT CTCCCTTTCG CGTACGACAT CCTCACCCCA GTCTTCCAAT
       ACGGCAATCG

198    CGCTTTCGCC AAATACCCAC AAGATAT-
       TCC AGACTATTTT AAACAAACAT TCCCCGAAGG CTATTCTTGG AACGCTCTA TGACCTATGA
       AGATCATGGA

298    ATTTGTATCG CTACCTCCGA CATTAC-
       TATG GAAGGCGACT GTTTTATTTA TAAAATTCGC TTTGATGGAA CTAACTTCCC CCCGAACGGC
       CCTGTAATGC

398    AAAAGAAGAC CTTAAAATGG GAACCTAG-
       CA CCGAAAAAAT GTATGTACGC GACGGAGTTC TTAAGGGTGA CGTAAACATG GCACTTCTGC
       TCGAAGGAGG
```

TABLE OF DNA AND PROTEIN SEQUENCES

```
498     TGGACACTAC CGCTGCGATT TTAAAAC-
        CAC TTATAAAGCC AAAAAAGATG TTCGTCTTCC AGATGCACAC AAGGTGGACC ACCGCATTGA
        AATCCTGAGC

598     CACGATAAAG ATTATAATAA AGTTAAACTC TATGAACACG CCGAAGCCCG CTATTCTATG TTACCGTCTC AGGCTAAAGC TAGC eCGP2                                                                                    [SEQ ID NO: 2]
  1     ATGTCAG TAATTAAACC GGAAAT-
        GAAA ATTAAATTGC GTTTGGAAGG TGCCGTTAAC GGCCATGAAT TTGTAATTGA AGGAGAAGGA
        AAAGGCAAAC

98     CATTCGAAGG AACCCAGACC CTGGATT-
        TAA CCGTAAAAGA AGGCGCACCT CTCCCTTTCG CGTACGACAT CCTCACCCCA GCCTTCCAAT
        ACGGCAATCG

198     CGCTTTCGCC AAATACCCAA AAGATAT-
        TCC AGACTATTTT AAACAAACAT TCCCCGAAGG CTATTCTTGG GAACGCTCTA TGACCTATGA
        AGATCAAGGA

298     ATTTGTATCG CTACCTCCGA CATTAC-
        TATG GAAGGAGACT GTTTTTTTTA TAAAATTCGC TTTGATGGAA CTAACTTCCC CCCGAACGGC
        CCTGTAATGC

398     AAAAGAAGAC CTTAAAATGG GAACCTAG-
        CA CCGAAAAAAT GTATGTACGC GACGGAGTTC TTAAGGGTGA CGTAAACATG GCACTTCTGC
        TCGAAGGAGG

498     TGGACACTAC CGCTGCGATT TTAAAAC-
        CAC TTATAAAGCC AAAAAAGATG TTCGTCTTCC AGATGCACAC AAGGTGGACC ACCGCATTGA
        AATCCTGAGC

598     CACGATAAAG ATTATAATAA AGTTAAACTC TATGAACACG CCGAAGCCCG CTATTCTATG TTACCGTCTC AGGCTAAAGC TAGC eCGP13                                                                                   [SEQ ID NO: 3]
  1     ATGTCAG TAATTAAACC GGAAAT-
        GAAA ATTAAATTGC GTATGGAAGG TGCCGTTAAC GGCCATAAAT TTGTAATTGA AGGGGAAGGA
        AAAGGCAACC

98     CATTCGAAGG AACCCAGACC CTGGATT-
        TAA CCGTAAAGGA AGGCGCACCT CTCCCTTTCG CGTACGACAT CCTCACCCCA GTCTTCCAAT
        ACGGCAATCG

198     CGCTTTCACC AAATACCCAC AAGATAT-
        TCC AGACTATTTT AAACAAACAT TCCCCGAAGG CTATTCTTGG GAACGCTCTA TGACCTATGA
        AGATCATGGA

298     ATTTGTATCG CTACCTCCGA CATTAC-
        TATG GAAGGCGACT GTTTTATTTA TAAAATTCGC TTTGATGGAA CTAACTTCCC CCCAAACGGC
        CCTGTAATGC

398     AAAAGAAGAC CTTAAAATGG GAACCTAG-
        CA CCGAAAAAAT GTATGTACGC GACGGAGTTC TTAAGGGTGA CGTAAACATG GCACTTCTGC
        TCGAAGGAGG

498     TGGACACTAC CGCTGCGATT TTAAAAC-
        CAC TTATAAAGCC AAAAAAGATG TTCGTCTTCC AGGTGCACAC AAGGTGGACC ACCGCATTGA
        AATCCTGAGC

598     CACGATAAAG ATTATAATAA AGTTAAACTC TATGAACACG CCGAAGCCCG CTATTCTATG TTACCGTCTC AGGCTAAAGC TAGC eCGP23                                                                                   [SEQ ID NO: 4]
  1     ATGTCAG TAATTAAACC GGAAAT-
        GAAA ATTAAATTGC GTTTGGAAGG TGCCGTTAAC GGCCATGAAT TTGTAATTGA AGGAGAAGGA
        AAAGGCAAAC

98     CATTCGAAGG AACCCAGACC CTGGATT-
        TAA CCGTAAAAGA AGGCGCACCT CTCCCTTTCG CGTACGACAT CCTCACCCCA GCCTTCCAAT
        ACGGCAATCG

198     CGCTTTCACC AAATACCCAA AAGATAT-
        TCC AGACTATTTT AAACAAACAT TCCCCGAAGG CTATTCTTGG GAACGCTCTA TGACCTATGA
        AGATCAAGGA

298     ATTTGTATCG CTACCTCCGA CATTAC-
        TATG GAAGGAGACT GTTTTTTTTA TAAGATTCGC TTTGATGGAA CTAACTTCCC CCCGAACGGC
        CCTGTAATGC

398     AAAAGAAGAC CTTAAAATGG GAACCTAG-
        CA CCGAAAAAAT GTATGTACGC GACGGAGTTC TTAAGGGTGA CGTAAACATG GCACTTCTGC
        TCGAAGGAGG
```

TABLE OF DNA AND PROTEIN SEQUENCES

```
498     TGGACACTAC CGCTGCGATT TTAAAAC-
        CAC TTATAAAGCC AAAAAAGATG TTCGTCTTCC AGATGCACAC GAGGTGGACC ACCGCATTGA
        AATCCTGAGC

598     CACGATAAAG ATTATAATAA AGTTAAACTC TATGAACACG CCGAAGCCCG CTATTCTATG TTACCGTCTC AGGCTAAAGC TAGC
``` eCGP123                                                                                                 [SEQ ID NO: 5]
```
  1     ATGTCAG TAATTAAACC GGAAAT-
        GAAA ATTAAATTGC GTATGGAAGG TGCCGTTAAC GGCCATAAAT TTGTAATTGA AGGAGAAGGA
        ATAGGCAAAC

98     CATACGAAGG AACCCAGACC CTGGATT-
        TAA CCGTAAAAGA AGGCGCACCT CTCCCTTTCT CGTACGACAT CCTCACCCCA GCCTTCCAAT
        ACGGCAATCG

198     CGCTTTCACC AAATACCCAA AAGATAT-
        TCC AGACTATTTT AAACAAGCAT TCCCCGAAGG CTATTCTTGG GAACGCTCTA TGACCTATGA
        AGATCAAGGA

298     ATTTGTATCG CTACCTCCGA CATTAC-
        TATG GAAGGAGACT GTTTTTTTTA TAAGATTCGC TTTGATGGAA CTAACTTCCC CCCGAACGGC
        CCTGTAATGC

398     AAAAGAAGAC CTTAAAATGG GAACCTAG-
        CA CCGAAAAAAT GTATGTACGC GACGGAGTTC TTAAGGGTGA CGTAAACATG GCACTTCTGC
        TCGAAGGAGG

498     TGGACACTAC CGCTGCGATT TTAAAAC-
        CAC TTATAAAGCC AAAAAAGATG TTCGTCTTCC AGATGCACAC GAGGTGGACC ACCGCATTGA
        AATCCTGAGC

598     CACGATAAAG ATTATAATAA AGTTAGACTC TATGAACACG CCGAAGCCCG CTATTCTATG TTACCGTCTC AGGCTAAAGC TAGC
``` eCGP Amino Acid Sequence:

eCGP1                                                                                                   [SEQ ID NO: 6]
MSVIKPEMKIKLRMEGAVNGHKFVIEGEGKGNPFEGTQTLDLTVKEGAPLPFAYDILTPVFQYGNRAFAKYPQDIPD
YFKQTFPEGYSWERSMTYEDHGICIATSDITHEGDCFIYKIRFDGTNFPPNGPVMUKTLKWEPSTEKIIYVRDGVLK
GDVNMALLLEGGGHYRCDFKTTYKAKKDVRLPDAHKVDHRIEILSHDKDYNKVKLYEHAEARYSMLPSQAK eCGP2                                                                                                   [SEQ ID NO: 7]
MSVIKPEMKIKLRLEGAVNGHEFVIEGEGKGKPFEGTQTLDLTVKEGAPLPFAYDILTPAFQYGNRAFAKYPKDIPD
YFKQTFPEGYSWERSMTYEDQGICIATSKITMEGDCFFYKIRFDGTNFPPNGPVMQKKTLKWEPSTEKMYVRDGVLK
GDVNMALLLEGGGHYRCDFKTTYKAKKDVRLPDAHKVDHRIEILSHDKDYNKVKLYEHAEARYSMLPSQAK eCGP13                                                                                                  [SEQ ID NO: 8]
MSVIKPEMKIKLRMEGAVNGHKFVIEGEGKGNPFEGTQTLDLTVKEGAPLPFAYDILTPVFQYGNRAFTKYPQDIPD
YFKQTFPEGYSWERSMTYEDHGICIATSDITMEGDCFIYKIRFDGTNFPPNGPVMQKKTLKWEPSTEKMYVRDGVLK
GDVNMALLLEGGGHYRCDFKTTYKAKKDVRLPGAHKVDHRIEILSHDKDYNKVKLYEHAEARYSMLPSQAK eCGP23                                                                                                  [SEQ ID NO: 9]
MSVIKPENKIKLRLEGAVNGHEPVIEGEGKGKPFEGTOTLDLTVKEGAPLPFAYDILTPAFQYGNRAFTKYPKDIPD
YFKQTFPEGYSWERSMTYEDQGTCTATSDITMEGDCFFYKIRFDGTNFPPNGPVMQKKTLKWEPSTEKMYVRDGVLK
GDVNMALLLEGGGHYRCDFKTTYKARKDVRLPDAHEVDHRIEILSHDKDYNKVKLYEHAEARYSMLPSQAK eCGP123                                                                                                 [SEQ ID NO: 10]
MSVIKPEMKIRLRMEGAVNGHXFVIEGEGIGKPYEGTQTLDLTVKEGAPLPFSYDILTPAFQYGNRAFTKYPKDIPD
YFKQAFPEGYSWERSMTYEDQGICIATSDITMEGDCFFYKIRFDGTNFPPNGPVMQKKTLKWEPSTEKMYVRDGVLK
GDVNMALLLEGGGHYRCDFKTTYKAKKDVRLPDAHEVDHRIEILSHDKDYNKVKLYEHAEARYSMLPSQAK

LITERATURE CITED BY SUPERSCRIPT FOOTNOTES

1. Eijsink, V. G. et al. Rational engineering of enzyme stability. *J Biotechnol* 113, 105-120 (2004).
2. Heinis, C., Alessi, P. & Neri, D. Engineering a thermostable human prolyl endopeptidase for antibody-directed enzyme prodrug therapy. *Biochemistry* 43, 6293-6303 (2004).
3. Willuda, J. et al. High thermal stability is essential for tumor targeting of antibody fragments: engineering of a humanized anti-epithelial glycoprotein-2 (epithelial cell adhesion molecule) single-chain Fv fragment. *Cancer Res* 59, 5758-5767 (1999).
4. Binz, H. K. et al. High-affinity binders selected from designed ankyrin repeat protein libraries. *Nat Biotechnol* 22, 575-582 (2004).
5. Knappik, A. et al. Fully synthetic human combinatorial antibody libraries (HuCAL) based on modular consensus frameworks and CDRs randomized with trinucleotides. *J. Mol. Biol.* 296, 57-86 (2000).
6. Bloom, J. D., Labthavikul, S. T., Otey, C. R. & Arnold, F. H. Protein stability promotes evolvability. *Proc Natl Acad Sci USA* 103, 5869-5874 (2006).
7. Pedelacq, J. D., Cabantous, S., Tran, T., Terwilliger, T. C. & Waldo, G. S. Engineering and characterization of a superfolder green fluorescent protein. *Nat Biotechnol* 24, 79-88 (2006).

8. Arnold, F. H., Giver, L., Gershenson, A., Zhao, H. & Miyazaki, K. Directed evolution of mesophilic enzymes into their thermophilic counterparts. *Ann N Y Acad Sci* 870, 400-403 (1999).
9. Giver, L., Gershenson, A., Freskgard, P. O. & Arnold, F. H. Directed evolution of a thermostable esterase. *Proc Natl Acad Sci USA* 95, 12809-12813 (1998).
10. Palackal, N. et al. An evolutionary route to xylanase process fitness. *Protein Sci* 13, 494-503 (2004).
11. Fridjonsson, O., Watzlawick, H. & Mattes, R. Thermoadaptation of alpha-galactosidase AgaB1 in *Thermus thermophilus*. *J Bacteriol* 184, 3385-3391 (2002).
12. Nakamura, A., Takakura, Y., Kobayashi, H. & Hoshino, T. In vivo directed evolution for thermostabilization of *Escherichia coli* hygromycin B phosphotransferase and the use of the gene as a selection marker in the host-vector system of *Thermus thermophilus*. *J Biosci Bioeng* 100, 158-163 (2005).
13. Sieber, V., Pluckthun, A. & Schmid, F. X. Selecting proteins with improved stability by a phage-based method. *Nat Biotechnol* 16, 955-960 (1998).
14. Kristensen, P. & Winter, G. Proteolytic selection for protein folding using filamentous bacteriophages. *Fold Des* 3, 321-328 (1998).
15. Wunderlich, M. & Schmid, F. X. In vitro evolution of a hyperstable Gbeta1 variant. *J Mol Biol* 363, 545-557 (2006).
16. Wunderlich, M., Martin, A., Staab, C. A. & Schmid, F. X. Evolutionary protein stabilization in comparison with computational design. *J Mol Biol* 351, 1160-1168 (2005).
17. Wunderlich, M., Martin, A. & Schmid, F. X. Stabilization of the cold shock protein CspB from *Bacillus subtilis* by evolutionary optimization of Coulombic interactions. *J Mol Biol* 347, 1063-1076 (2005).
18. Martin, A., Schmid, F. X. & Sieber, V. Proside; a phage-based method for selecting thermostable proteins. *Methods Mol Biol* 230, 57-70 (2003).
19. Martin, A. & Schmid, F. X. Evolutionary stabilization of the gene-3-protein of phage fd reveals the principles that govern the thermodynamic stability of two-domain proteins. *J Mol Biol* 328, 863-875 (2003).
20. Martin, A., Sieber, V. & Schmid, F. X. In-vitro selection of highly stabilized protein variants with optimized surface. *J Mol Biol* 309, 717-726 (2001).
21. Shusta, E. V., Kieke, M. C., Parke, E., Kranz, D. M. & Wittrup, K. D. Yeast polypeptide fusion surface display levels predict thermal stability and soluble secretion efficiency. *J. Mol. Biol.* 292, 949-956 (1999).
22. Park, S. et al. Limitations of yeast surface display in engineering proteins of high thermostability. *Protein Eng Des Sel* 19, 211-217 (2006).
23. Steipe, B. Consensus-based engineering of protein stability: from intrabodies to thermostable enzymes. *Methods Enzymol* 388, 176-186 (2004).
24. Steipe, B., Schiller, B., Pluckthun, A. & Steinbacher, S. Sequence statistics reliably predict stabilizing mutations in a protein domain. *J. Mol. Biol.* 240, 188-192 (1994).
25. Ohage, E. & Steipe, B. Intrabody construction and expression, I. The critical role of VL domain stability. *J. Mol. Biol.* 291, 1119-1128 (1999).
26. Wirtz, P. & Steipe, B. Intrabody construction and expression III: engineering hyperstable V(H) domains. *Protein Sci.* 8, 2245-2250 (1999).
27. Visintin, M. et al. The intracellular antibody capture technology (IACT): towards a consensus sequence for intracellular antibodies. *J. Mol. Biol.* 317, 73-83 (2002).
28. Arndt, M. A. et al. Generation of a highly stable, internalizing anti-CD22 single-chain Fv fragment for targeting non-Hodgkin's lymphoma. *Int J Cancer* 107, 822-829 (2003).
29. McDonagh, C. F. et al. Improved yield and stability of L49-sFv-beta-lactamase, a single-chain antibody fusion protein for anticancer prodrug activation, by protein engineering. *Bioconjug Chem* 14, 860-869 (2003).
30. Whitcomb, E. A., Martin, T. M. & Rittenberg, M. B. Restoration of Ig secretion: mutation of germline-encoded residues in T15L chains leads to secretion of free light chains and assembled antibody complexes bearing secretion-impaired heavy chains. *J Immunol* 170, 1903-1909 (2003).
31. Demarest, S. J., Rogers, J. & Hansen, G. Optimization of the antibody C(H)3 domain by residue frequency analysis of IgG sequences. *J Mol Biol* 335, 41-48 (2004).
32. Wang, Q., Buckle, A. M. & Fersht, A. R. Stabilization of GroEL minichaperones by core and surface mutations. *J Mol Biol* 298, 917-926 (2000).
33. Wang, Q., Buckle, A. M., Foster, N. W., Johnson, C. M. & Fersht, A. R. Design of highly stable functional GroEL minichaperones. *Protein Sci* 8, 2186-2193 (1999).
34. Nikolova, P. V., Henckel, J., Lane, D. P. & Fersht, A. R. Semirational design of active tumor suppressor p53 DNA binding domain with enhanced stability. *Proc Natl Acad Sci USA* 95, 14675-14680 (1998).
35. Jiang, X., Kowalski, J. & Kelly, J. W. Increasing protein stability using a rational approach combining sequence homology and structural alignment: Stabilizing the WW domain. *Protein Sci* 10, 1454-1465 (2001).
36. Maxwell, K. L. & Davidson, A. R. Mutagenesis of a buried polar interaction in an SH3 domain: sequence conservation provides the best prediction of stability effects. *Biochemistry* 37, 16172-16182 (1998).
37. Lehmann, M. et al. The consensus concept for thermostability engineering of proteins: further proof of concept. *Protein Eng* 15, 403-411 (2002),
38. Lehmann, M. & Wyss, M. Engineering proteins for thermostability: the use of sequence alignments versus rational design and directed evolution. *Curr Opin Biotechnol* 12, 371-375 (2001).
39. Lehmann, M., Pasamontes, L., Lassen, S. F. & Wyss, M. The consensus concept for thermostability engineering of proteins. *Biochim Biophys Acta* 1543, 408-415 (2000).
40. Lehmann, M. et al. From DNA sequence to improved functionality: using protein sequence comparisons to rapidly design a thermostable consensus phytase. *Protein Eng* 13, 49-57 (2000).
41. Devi, V. S. et al. Folding of a designed simple ankyrin repeat protein. *Protein Sci* 13, 2864-2870 (2004).
42. Kohl, A. et al. Designed to be stable: Crystal structure of a consensus ankyrin repeat protein. *Proc Natl Aced Sci USA* 100, 1700-1705 (2003).
43. Main, E. R., Jackson, S. E. & Regan, L. The folding and design of repeat proteins: reaching a consensus. *Curr Opin Struct Biol* 13, 482-489 (2003).
44. Dai, M. et al. The creation of a novel fluorescent protein by guided consensus engineering. *Protein Eng Des Sel* 20, 69-79 (2007).
45. Karasawa, S., Araki, T., Yamamoto-Hino, M. & Miyawaki, A. A green-emitting fluorescent protein from Galaxeidae coral and its monomeric version for use in fluorescent labeling. *J Biol Chem* 278, 34167-34171 (2003).
46. Serrano, L. & Fersht, A. R. Capping and alpha-helix stability. *Nature* 342, 296-299 (1989).

47. Sali, D., Bycroft, M. & Fersht, A. R. Stabilization of protein structure by interaction of alpha-helix dipole with a charged side chain. *Nature* 335, 740-743 (1988).
48. Nicholson, H., Becktel, W. J. & Matthews, B. W. Enhanced protein thermostability from designed mutations that interact with alpha-helix dipoles. *Nature* 336, 651-656 (1988).
49. Nicholson, H., Anderson, D. E., Dao-pin, S. & Matthews, B. W. Analysis of the interaction between charged side chains and the alpha-helix dipole using designed thermostable mutants of phage T4 lysozyme. *Biochemistry* 30, 9816-9828 (1991).
50. Blaber, M., Zhang, X. J. & Matthews, B. W. Structural basis of amino acid alpha helix propensity. *Science* 260, 1637-1640 (1993).
51. Serrano, L., Sancho, J., Hirshberg, M. & Fersht, A. R. Alpha-helix stability in proteins. I. Empirical correlations concerning substitution of side-chains at the N and C-caps and the replacement of alanine by glycine or serine at solvent-exposed surfaces. *J Mol Biol* 227, 544-559 (1992).
52. Serrano, L., Neira, J. L., Sancho, J. & Fersht, A. R. Effect of alanine versus glycine in alpha-helices on protein stability. *Nature* 356, 453-455 (1992).
53. Schwehm, J. M., Fitch, C. A., Dang, B. N., Garcia-Moreno, E. B. & Stites, W. E. Changes in stability upon charge reversal and neutralization substitution in staphylococcal nuclease are dominated by favorable electrostatic effects. *Biochemistry* 42, 1118-1128 (2003).
54. Makhatadze, G. I., Loladze, V. V., Emolenko, D. N., Chen, X. & Thomas, S. T. Contribution of surface salt bridges to protein stability: guidelines for protein engineering. *J Mol Biol* 327, 1135-1148 (2003).
55. Pace, C. N., Alston, R. W. & Shaw, K. L. Charge-charge interactions influence the denatured state ensemble and contribute to protein stability. *Protein Sci* 9, 1395-1398 (2000).
56. Strop, P. & Mayo, S. L. Contribution of surface salt bridges to protein stability. *Biochemistry* 39, 1251-1255 (2000).
57. Waldburger, C. D., Schildbach, J. F. & Sauer, R. T. Are buried salt bridges important for protein stability and conformational specificity? *Nat Struct Biol* 2, 122-128 (1995).
58. Dao-pin, S. et al. Structural and genetic analysis of electrostatic and other interactions in bacteriophage T4 lysozyme. *Ciba Found Symp* 161, 52-62 (1991).
59. Serrano, L., Horovitz, A., Avron, B., Bycroft, M. & Fersht, A. R. Estimating the contribution of engineered surface electrostatic interactions to protein stability by using double-mutant cycles. *Biochemistry* 29, 9343-9352 (1990).
60. Anderson, D. E., Hurley, J. H., Nicholson, H., Baase, W. A. & Matthews, B. W. Hydrophobic core repacking and aromatic-aromatic interaction in the thermostable mutant of T4 lysozyme Ser 117-->Phe. *Protein Sci* 2, 1285-1290 (1993).
61. Serrano, L., Bycroft, M. & Fersht, A. R. Aromatic-aromatic interactions and protein stability. Investigation by double-mutant cycles. *J Mol Biol* 218, 465-475 (1991).
62. Burley, S. K. & Petsko, G. A. Aromatic-aromatic interaction: a mechanism of protein structure stabilization. *Science* 229, 23-28 (1985).
63. Matsumura, M., Signor, G. & Matthews, B. W. Substantial increase of protein stability by multiple disulphide bonds. *Nature* 342, 291-293 (1989).
64. Matthews, B. W., Nicholson, H. & Becktel, W. J. Enhanced protein thermostability from site-directed mutations that decrease the entropy of unfolding. *Proc Natl Acad Sci USA* 84, 6663-6667 (1987).
65. Clarke, J. & Fersht, A. R. Engineered disulfide bonds as probes of the folding pathway of barnase: increasing the stability of proteins against the rate of denaturation. *Biochemistry* 32, 4322-4329 (1993).
66. Morea, V., Tramontano, A., Rustici, M., Chothia, C. & Lesk, A. M. Conformations of the third hypervariable region in the VH domain of immunoglobulins. *J. Mol. Biol.* 275, 269-294 (1998).
67. Lefranc, M. P. et al. IMGT unique numbering for immunoglobulin and T cell receptor constant domains and Ig superfamily C-like domains. *Dev Comp Immunol* 29, 185-203 (2005).
68. Ward, W. W. & Bokman; S. H. Reversible denaturation of Aequorea green-fluorescent protein: physical separation and characterization of the renatured protein. *Biochemistry* 21, 4535-4540 (1982).
69. Bokman, S. H. & Ward, W. W. Renaturation of Aequorea green fluorescent protein. *Biochem Biophys Res Commun* 101, 1372-1380 (1981).
70. Binz, Stumpp, M. T., Forrer, P., Amstutz, P. & Pluckthun, A. Designing repeat proteins: well-expressed, soluble and stable proteins from combinatorial libraries of consensus ankyrin repeat proteins, *J Mol Biol* 332, 489-503 (2003).
71. Ericsson, U. B., Hallberg, B. M., Detitta, G. T., Dekker, N. & Nordlund, P. Thermofluor-based high-throughput stability optimization of proteins for structural studies. *Anal Biochem* 357, 289-298 (2006).
72. Cummings, M. D., Famum, M. A. & Nelen, M. I. Universal screening methods and applications of ThermoFluor. *J Biomol Screen* 11, 854-863 (2006).
73. Li, W. F., Zhou, X. X. & Lu, P. Structural features of thermozymes. *Biotechnol Adv* 23, 271-281 (2005).
74. Daniel, R. M., Dines, M. & Petach, H. H. The denaturation and degradation of stable enzymes at high temperatures. *Biochem J* 317 (Pt 1), 1-11 (1996).
75. Chou, P. Y. & Fasman, G. D. Empirical predictions of protein conformation. *Annu Rev Biochem* 47, 251-276 (1978).
76. Chen, H., Gu, F. & Huang, Z. Improved Chou-Fasman method for protein secondary structure prediction. *BMC Bioinformatics* 7 Suppl 4, S14 (2006).
77. Ginalski, K, Grishin, N. V., Godzik, A. & Rychlewski, L. Practical lessons from protein structure prediction. *Nucleic Acids Res* 33, 1874-1891 (2005).
78. Dunbrack, R. L., Jr. Sequence comparison and protein structure prediction. *Curr Opin Struct Biol* 16, 374-384 (2006).
79. Jespers, L., Jenne, S., Lasters, I. & Collen, D. Epitope mapping by negative selection of randomized antigen libraries displayed on filamentous phage. *J. Mol. Biol.* 269, 704-718 (1997).
80. Pannekoek, H., van Meijer, M., Schleef, R. R., Loskutoff, D. J. & Barbas, C. d. Functional display of human plasminogen-activator inhibitor 1 (PAI-1) on phages: novel perspectives for structure-function analysis by error-prone DNA synthesis. *Gene* 128, 135-140 (1993).
81. van Meijer, M. et al. Selective screening of a large phage display library of plasminogen activator inhibitor 1 mutants to localize interaction sites with either thrombin or the variable region 1 of tissue-type plasminogen activator. *J. Biol. Chem.* 271, 7423-7428 (1996).

82. Oliphant, T. et al. Development of a humanized monoclonal antibody with therapeutic potential against West Nile virus. *Nat Med* 11, 522-530 (2005).
83. Levy, R. et al. Fine and domain-level epitope mapping of botulinum neurotoxin type A neutralizing antibodies by yeast surface display. *J Mol Biol* 365, 196-210 (2007).
84. Chao, G., Cochran, J. R. & Wittrup, K. D. Fine epitope mapping of anti-epidermal growth factor receptor antibodies through random mutagenesis and yeast surface display. *J Mol Biol* 342, 539-550 (2004).
85. Johns, T. G. et al. Identification of the epitope for the epidermal growth factor receptor-specific monoclonal antibody 806 reveals that it preferentially recognizes an untethered form of the receptor. *J Biol Chem* 279, 30375-30384 (2004).
87. Ward, W. W. & Bokman, S. H. Reversible denaturation of Aequorea green-fluorescent protein: physical separation and characterization of the renatured protein. *Biochemistry* 21, 4535-4540 (1982).
88. Kiss, C. et al. Antibody binding loop insertions as diversity elements. *Nucleic Acids Res* 34, e132 (2006).
89. Lesley, S. A. et al. Structural genomics of the *Thermotoga maritima* proteome implemented in a high-throughput structure determination pipeline. *Proc. Natl. Acad. Sci. U.S.A.* 99, 11664-11669 (2002).
90. Wilmann, P. G. et al. The 1.7 A crystal structure of Dronpa: a photoswitchable green fluorescent protein. *J Mol Biol* 364, 213-224 (2006).
91. Zhao, H. & Arnold, F. H. Optimization of DNA shuffling for high fidelity recombination. *Nucleic Acids Res* 25, 1307-1308 (1997):

What is claimed is:

1. A nucleic acid molecule comprising a polynucleotide encoding the polypeptide having the amino acid sequence of SEQ ID NO: 9.

2. The nucleic acid molecule of claim 1, wherein the amino acid sequence of SEQ ID NO: 9 is encoded by the polynucleotide of SEQ ID NO: 4.

3. The nucleic acid molecule of claim 2, which is a vector.

4. The nucleic acid molecule of claim 2, which is an expression vector.

5. A host cell comprising the nucleic acid molecule of claim 1.

6. A host cell comprising the vector of claim 3.

7. A host cell comprising the expression vector of claim 4.

8. A method of making a polypeptide having the amino acid sequence of SEQ ID NO: 9, the method comprising expressing the nucleic acid molecule of claim 1.

9. The method of claim 8, wherein the nucleic acid molecule is expressed in a host cell.

10. The method of claim 8, wherein the nucleic acid molecule comprises the sequence of SEQ ID NO: 4.

11. The method of claim 8, wherein the nucleic acid molecule is a vector.

12. The method of claim 8, further comprising isolating the expressed polypeptide.

13. A method of making a fluorescent polypeptide, comprising growing the host cell of claim 7 under conditions sufficient to express the polypeptide with the amino acid sequence of SEQ ID NO: 9.

* * * * *